United States Patent
Itabashi et al.

(10) Patent No.: US 9,472,766 B2
(45) Date of Patent: Oct. 18, 2016

(54) FUSED POLYCYCLIC COMPOUND AND ORGANIC LIGHT EMITTING ELEMENT INCLUDING THE SAME

(71) Applicant: CANON KABUSHIKI KAISHA, Tokyo (JP)

(72) Inventors: Masumi Itabashi, Kodaira (JP); Hiroki Ohrui, Kawasaki (JP); Hironobu Iwawaki, Yokohama (JP); Kei Tagami, Yokohama (JP); Tetsuo Takahashi, Kawasaki (JP); Kenichi Ikari, Abiko (JP); Ryuji Ishii, Yokohama (JP); Masanori Muratsubaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/767,898

(22) PCT Filed: Jan. 29, 2014

(86) PCT No.: PCT/JP2014/052598
§ 371 (c)(1),
(2) Date: Aug. 13, 2015

(87) PCT Pub. No.: WO2014/125970
PCT Pub. Date: Aug. 21, 2014

(65) Prior Publication Data
US 2016/0035982 A1 Feb. 4, 2016

(30) Foreign Application Priority Data
Feb. 15, 2013 (JP) .................. 2013-027778

(51) Int. Cl.
| | | |
|---|---|---|
| *H01L 51/00* | (2006.01) | |
| *C07C 255/51* | (2006.01) | |
| *C07D 235/20* | (2006.01) | |
| *C07C 13/62* | (2006.01) | |
| *C07C 22/08* | (2006.01) | |
| *C07C 25/22* | (2006.01) | |
| *C09K 11/06* | (2006.01) | |
| *C07D 215/06* | (2006.01) | |
| *C07D 235/18* | (2006.01) | |
| *C07D 213/06* | (2006.01) | |
| *G03G 15/04* | (2006.01) | |
| *G09G 3/32* | (2016.01) | |
| *H01L 27/32* | (2006.01) | |
| *H05B 33/08* | (2006.01) | |
| *H01L 51/50* | (2006.01) | |

(52) U.S. Cl.
CPC ........... *H01L 51/0056* (2013.01); *C07C 13/62* (2013.01); *C07C 22/08* (2013.01); *C07C 25/22* (2013.01); *C07C 255/51* (2013.01); *C07D 213/06* (2013.01); *C07D 215/06* (2013.01); *C07D 235/18* (2013.01); *C07D 235/20* (2013.01); *C09K 11/06* (2013.01); *G03G 15/04054* (2013.01); *G09G 3/3225* (2013.01); *H01L 27/3248* (2013.01); *H01L 51/0067* (2013.01); *H01L 51/0072* (2013.01); *H05B 33/0896* (2013.01); *C07C 2103/18* (2013.01); *C07C 2103/54* (2013.01); *C09K 2211/1007* (2013.01); *C09K 2211/1011* (2013.01); *C09K 2211/1029* (2013.01); *C09K 2211/1044* (2013.01); *G09G 2300/08* (2013.01); *H01L 51/006* (2013.01); *H01L 51/0054* (2013.01); *H01L 51/5012* (2013.01); *H01L 51/5024* (2013.01)

(58) Field of Classification Search
CPC ........... H01L 51/0056; H01L 51/0072; H01L 51/0067; H01L 51/0054; H01L 51/006; H01L 51/5012; H01L 51/5024; H01L 27/3248; C07C 255/51; C07C 13/62; C07C 22/08; C09K 11/06; G03G 15/04054; G03G 3/3225
See application file for complete search history.

(56) References Cited

FOREIGN PATENT DOCUMENTS

| | | | |
|---|---|---|---|
| JP | 11-040360 | A | 2/1999 |
| JP | 2003-238516 | A | 8/2003 |
| JP | 2003238516 | * | 8/2003 |
| JP | 2010-143880 | A | 7/2010 |
| WO | 2011/145637 | A1 | 11/2011 |

* cited by examiner

*Primary Examiner* — D M Seaman
(74) *Attorney, Agent, or Firm* — Canon U.S.A. Inc., IP Division

(57) ABSTRACT

The present invention provides a novel fused polycyclic compound suitably used for a blue light emitting element and an organic light emitting element including the fused polycyclic compound.
A fused polycyclic compound is represented by at least one of the general formulas [1] and [2] according to claim 1. In the general formulas [1] and [2], $R_1$ to $R_{20}$ each represent a hydrogen atom or a substituent.

20 Claims, 1 Drawing Sheet

FUSED POLYCYCLIC COMPOUND AND ORGANIC LIGHT EMITTING ELEMENT INCLUDING THE SAME

TECHNICAL FIELD

The present invention relates to a novel fused polycyclic compound and an organic light emitting element including the same.

BACKGROUND ART

An organic light emitting element is an element which includes a thin film containing a fluorescent or a phosphorescent organic compound between a pair of electrodes, which generates excitons of the fluorescent or the phosphorescent organic compound by injecting electrons and holes (positive holes) from the respective electrodes, and which uses light emitted when the excitons are returned to the ground state.

Since advancement of organic light emitting elements has been significantly carried out, a thin and a lightweight light emitting device having features, such as a high luminance at a low application voltage, various light emission wavelengths, and a high speed response, may be probably realized. Hence, the organic light emitting element is expected to be widely applied to various types of applications.

In PTL 1 and PTL 2, a compound which emits blue light only by its basic skeleton has been disclosed. In PTL 1, a basic skeleton represented by the following structural formula 1 has been disclosed. In PTL 2, a basic skeleton represented by the following structural formula 2 has been disclosed.

[Chem. 1]

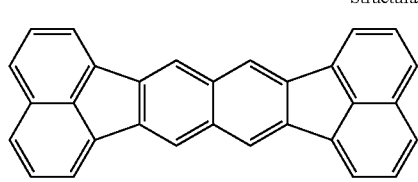

Structural formula 1

[Chem. 2]

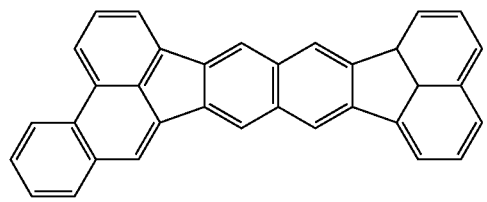

Structural formula 2

CITATION LIST

Patent Literature

PTL 1 Japanese Patent Laid-Open No. 11-40360
PTL 2 Japanese Patent Laid-Open No. 2010-143880

SUMMARY OF INVENTION

An organic light emitting element preferably has a high light emission efficiency. Hence, a light emitting material of the organic light emitting element preferably has a high oscillator strength. In addition, a material emitting blue light is particularly required to have a high light emission efficiency.

Accordingly, the present invention provides a compound which emits blue light having a high color purity and which has a high oscillator strength. In addition, the present invention also provides an organic light emitting element which includes the compound described above and which has a high light emission efficiency and a high durability.

Hence, the present invention provides a fused polycyclic compound represented by the following general formula [1] or [2].

[Chem. 3]

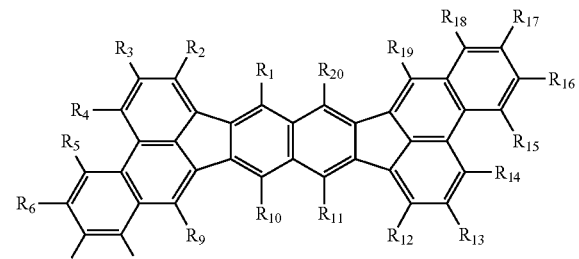

[1]

[Chem. 4]

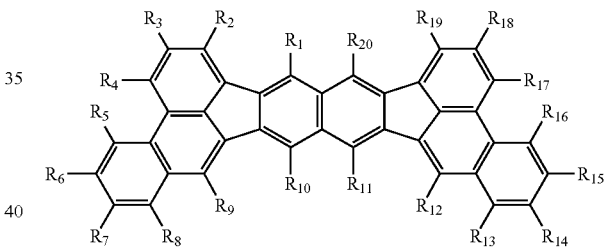

[2]

In the general formulas [1] and [2], $R_1$ to $R_{20}$ are each independently selected from the group consisting of a hydrogen atom, a cyano group, a substituted or an unsubstituted alkyl group, a substituted or an unsubstituted aryl group, and a substituted or an unsubstituted heterocyclic group.

Advantageous Effects of Invention

According to the present invention, an organic compound which emits blue light having a high color purity and which has a high oscillator strength can be provided. In addition, an organic light emitting element which includes the above organic compound and which has a high light emission efficiency and a superior durability can also be provided.

Further features of the present invention will become apparent from the following description of exemplary embodiments with reference to the attached drawings.

DESCRIPTION OF EMBODIMENTS

Figure 1:
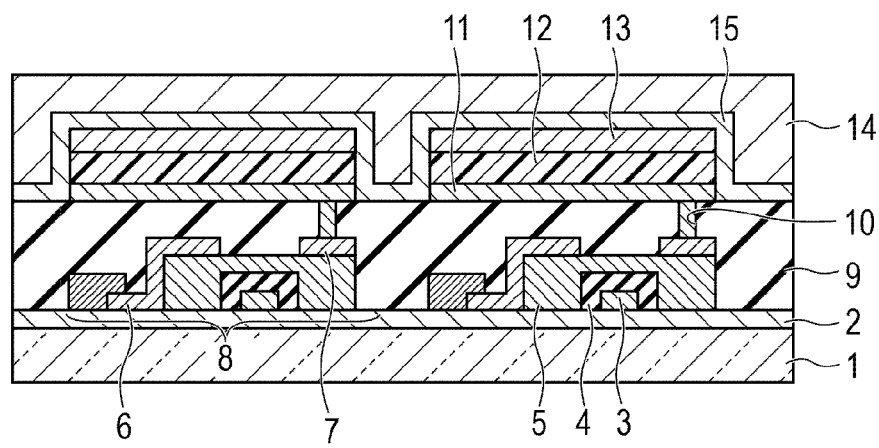
FIG. 1 is a schematic cross-sectional view showing one example of a display device including an organic light emitting element of the present invention and an active element connected thereto.
Figure 2:
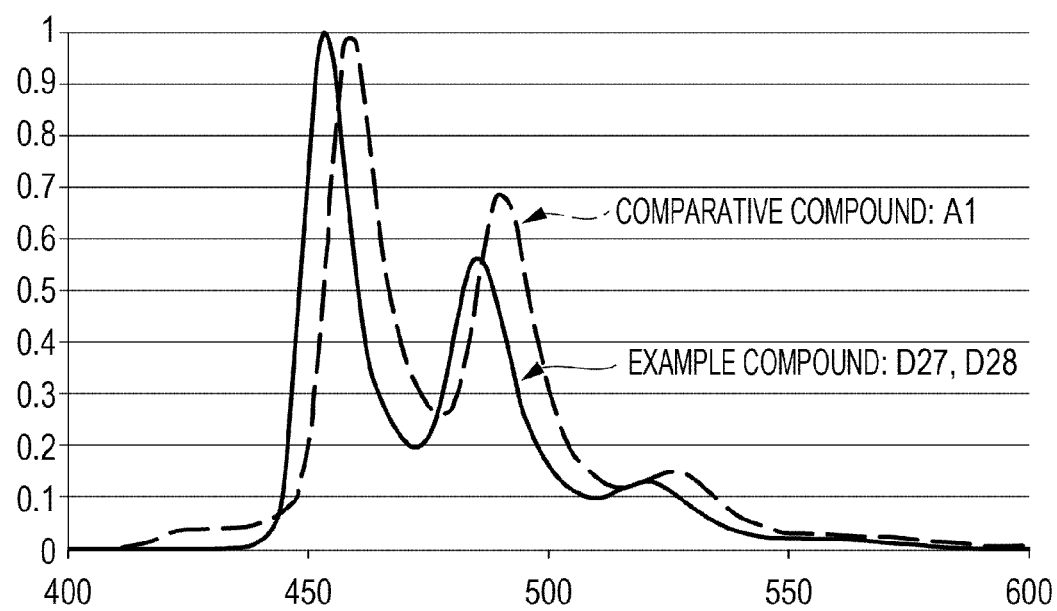
FIG. 2 is a graph showing spectra of photoluminescence of a mixture of example compounds D27 and D28 and that of a comparative compound A1.

[1] Fused Polycyclic Compound of the Present Invention

A naphtho[2,3-e:6,7-e']diacephenanthrylene compound and a naphtho[2,3-e:7,6-e']diacephenanthrylene compound are compounds represented by the following general formulas [1] and [2], respectively.

[Chem. 5]

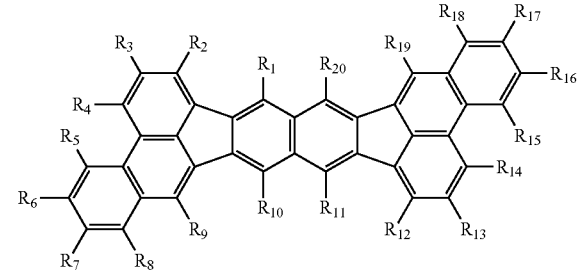

[1]

[Chem. 6]

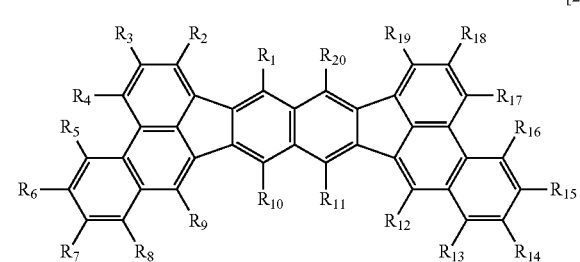

[2]

In the general formulas [1] and [2], $R_1$ to $R_{20}$ are each independently selected from the group consisting of a hydrogen atom, a cyano group, a substituted or an unsubstituted alkyl group, a substituted or an unsubstituted aryl group, and a substituted or an unsubstituted heterocyclic group.

In the general formulas [1] and [2], as the substituted or the unsubstituted alkyl group, although a methyl group, an ethyl group, a n-propyl group, a n-butyl group, n-pentyl group, a n-hexyl group, a n-heptyl group, a n-octyl group, a n-decyl group, an iso-propyl group, an iso-butyl group, a sec-butyl group, a tert-butyl group, an iso-pentyl group, a neopentyl group, a tert-octyl group, a fluoromethyl group, a difluoromethyl group, a trifluoromethyl group, 2-fluoroethyl group, a 2,2,2-trifluoroethyl group, a perfluoroethyl group, 3-fluoropropyl group, a perfluoropropyl group, a 4-fluorobutyl group, a perfluorobutyl group, a 5-fluoropentyl group, a 6-fluorohexyl group, a cyclopropyl group, a cyclobutyl group, a cyclopentyl group, a cyclohexyl group, a cyclopentylmethyl group, a cyclohexylmethyl group, a cyclohexylethyl group, 4-fluorocyclohexyl group, a norbornyl group, and an adamanthyl group may be mentioned by way of example, of course, the substituted or the unsubstituted alkyl group is not limited to those mentioned above.

In the general formulas [1] and [2], as the aryl group, although a phenyl group, a naphthyl group, an indenyl group, a biphenyl group, a terphenyl group, a fluorenyl group, an anthryl group, a phenanthryl group, a pyrenyl group, a tetracenyl group, a pentacenyl group, a triphenyl group, and a perylenyl group may be mentioned by way of example, of course, the aryl group is not limited to those mentioned above.

In the general formulas [1] and [2], as the heterocyclic group, although a thienyl group, a pyrrolyl group, a pyridyl group, a pyrazyl group, a pyrimidyl group, a pyridazinyl group, a quinolinyl group, an isoquinolinyl group, an oxazolyl group, an oxadiazolyl group, a phenanthridinyl group, an acridinyl group, a naphthyridinyl group, a quinoxalinyl group, a quinazolinyl group, a cinnolinyl group, a phthalazinyl group, a phenanthrolyl group, a phenazinyl group, a dibenzofuranyl group, a dibenzothiophenyl group, a carbazolyl group, a benzofuranyl group, a benzothiophenyl group, an indolyl group, a cycloazyl group, a benzoimidazolyl group, a benzothiazolyl group, and a benzothiadiazolyl group may be mentioned by way of example, of course, the heterocyclic group is not limited to those mentioned above.

In the general formulas [1] and [2], as the substitute, that is, as the substitute of the alkyl group, the aryl group, or the heterocyclic group, although an alkyl group, such as a methyl group, an ethyl group, a propyl group, or a butyl group; an aralkyl group, such as a benzyl group; an aryl group, such as a phenyl group or a biphenyl group; a heterocyclic group, such as a pyridyl group, a pyrrolyl group, a benzoimidazolyl group, or a benzothiazolyl group; an amino group, such as a dimethylamino group, a diethylamino group, a dibenzylamino group, a diphenylamino group, or a ditolylamino group; an alkoxy group, such as a methoxy group, an ethoxy group, a propoxy group, or a phenoxy group; a cyano group; and a halogen atom, such as fluorine, chlorine, bromine, or iodine, may be mentioned by way of example, of course, the substituent is not limited to those mentioned above.

In the general formulas [1] and [2] of the present invention, at least two of $R_1$, $R_{10}$, $R_{11}$, and $R_{20}$ more preferably represent electron withdrawing substitutes. In addition, $R_1$ and $R_{10}$ or $R_{11}$ and $R_{20}$ are even more preferably used in combination.

In this embodiment, as the electron withdrawing substitute, although a cyano group, a nitro group, an alkyl sulfonyl group, an halogenated alkyl group, a halogenated phenyl group, an acyl group, an alkoxycarbonyl group, a sulfamoyl group, a carbamoyl group, a halogenated alkoxy group, a sulfonyloxy group, a halogenated alkylthio group, a benzonitrile group, a pyridyl group, a quinolyl group, an isoquinolyl group, a benzoxazolyl group, a benzothiazolyl group, a phenylbenzothiazolyl group, a benzimidazolyl group, an oxazolopyridyl group, and a halogen atom may be mentioned by way of example, of course, the electron withdrawing substitute is not limited to those mentioned above.

In this embodiment, the basic skeleton indicates the structure formed only by fused rings. In a naphtho[2,3-e:6,7-e']diacephenanthrylene compound and a naphtho[2,3-e:7,6-e']diacephenanthrylene compound of this embodiment, the structure of a compound in which $R_1$ to $R_{20}$ of the formulas [1] and [2] all represent hydrogen atoms corresponds to the basic skeleton of this embodiment.

Hereinafter, the compound of this embodiment will be described in more detail.

In general, in order to increase the light emission efficiency of an organic light emitting element, the light emission quantum yield of its light emission center itself is desirably high. Hence, the following two points are preferably satisfied.

(A) High oscillator strength
(B) Small number of oscillation portions of a skeleton relating to the light emission Hereinafter, those two points will be described in detail.

(A) High Oscillator Strength

It is important to improve the symmetry of a skeleton relating to the light emission of a molecule. However, depending on a specific forbidden transition condition of a high symmetric molecule, no light emission may occur in some cases.

As a method to increase the oscillator strength, a method may be mentioned in which the direction of the longest conjugated plane is regarded as an axis, and the conjugation sequence is further expanded along this axis direction. As a result, the dipole moment of the molecule is increased, and hence the oscillator strength is increased.

The case of the compound represented by the general formula [1] or [2] of the present invention, the direction of the longest conjugated plane of the basic skeleton is regarded as an X axis direction, and the moment is preferably increased in this direction.

On the other hand, when the fused ring structure is expanded in order to increase the moment in the X axis direction, the light emission wavelength may be increased in some cases. Hence, in order to suppress the increase in light emission wavelength, the direction in which the fused ring structure of the fused polycyclic compound of the present invention is expanded is slightly shifted from the X axis direction.

That is, the fused polycyclic compound of the present invention has the structure that simultaneously satisfies light emission in a blue light region and a high oscillator strength.

In addition, the blue light region in this embodiment is a region of 430 to 480 nm, and a more preferable blue light region is a region of 440 to 460 nm. The preferable blue light region indicates a region having a superior color purity.

The following table shows the results of the oscillator strength used as an index of the quantum yield obtained by quantum chemical calculation at B3LYP/6-31G* level using the Density Functional Theory.

TABLE 1

| No. | STRUCTURAL FORMULA | OSCILLATOR STRENGTH | MAXIMUM LIGHT EMISSION WAVELENGTH [nm] |
|---|---|---|---|
| 1 | | 0.555 | 433 |
| 2 | | 0.559 | 432 |
| 3 | | 0.491 | 433 |
| 4 | | 0.364 | 428 |

In naphtho[2,3-e:6,7-e']diacephenanthrylene (Table 1, No. 1) and naphtho[2,3-e:7,6-e']diacephenanthrylene (Table 1, No. 2), the oscillator strength is increased while the maximum light emission wavelength is maintained in a blue light region as compared to that of fluorantheno[8,9-k] fluoranthene (Table 1, No. 3).

In the general formula [3], the number of the substitution position of fluorantheno[8,9-k] fluoranthene is shown. In fluorantheno[8,9-k] fluoranthene (Table 1, No. 3), the reactivities of hydrogen atoms located at the 3-, 4-, 11-, and 12-positions are high.

Hence, when an organic light emitting element is driven to emit light, the compound in the element is degraded by a radical reaction, and it is believed that this degradation is one of causes to decrease an element durability life.

Accordingly, when those positions described above are protected and stabilized by carbon bonds, improvement in element durability life may be expected.

Hence, in the present invention, when there is formed a structure represented by the general formula [1] which has fused rings on fluorantheno[8,9-k]fluoranthene represented by the general formula [3] in directions toward the 2- and 3-positions and the 10- and 11-positions or in directions toward the 4- and 5-positions and the 12- and 13-positions so as to expand the conjugation sequence, or when there is formed a structure represented by the general formula [2] which has fused rings on fluorantheno[8,9-k]fluoranthene represented by the general formula [3] in directions toward the 2- and 3-positions and the 12- and 13-positions or in directions toward the 4- and 5-positions and the 10- and 11-positions so as to expand the conjugation sequence, the stability of the fused polycyclic compound is improved, and hence the element durability life can be improved.

[Chem. 7]

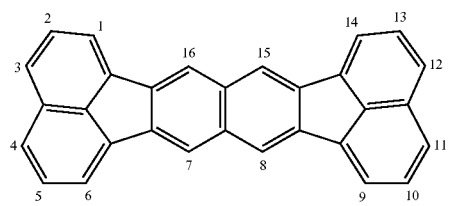

[3]

However, in the fused polycyclic compound of this embodiment, the fused rings are boned to only two positions among the four high reactive positions of fluorantheno[8,9-k]fluoranthene. It is estimated that when all the four positions are blocked by carbon bonds, the stability as a fused polycyclic compound is improved (Table 1, No. 4).

However, it was suggested by the result obtained from the quantum chemical calculation that when the four positions are blocked as shown in Table 1, since the symmetry of the fused polycyclic compound is increased, the oscillator strength is decreased.

(B) Small Number of Oscillation Portions of Skeleton Relating to Light Emission

When the skeleton relating to light emission has no rotational structure, a decrease in quantum yield caused by rotational oscillation can be suppressed. Since the naphtho[2,3-e:6,7-e']diacephenanthrylene skeleton and the naphtho[2,3-e:7,6-e']diacephenanthrylene skeleton represented by the general formulas [1] and [2], respectively, of the present invention each have no rotational axis, a decrease in quantum yield caused by vibrational deactivation is small, and hence the skeletons described above are each preferable as a light emitting material.

When the naphtho[2,3-e:6,7-e']diacephenanthrylene skeleton and the naphtho[2,3-e:7,6-e']diacephenanthrylene skeleton of the present invention each have a high planarity and are not substituted, excimers are liable to be generated.

Hence, in order to suppress the generation of excimers, substituents are preferably provided. As particular substitution positions, the substituents are preferably provided in a symmetric manner at $R_1$, $R_{10}$, $R_{11}$, and $R_{20}$ of the above general formulas [1] and [2]. In addition, the substituents are more preferably provided at $R_1$ and $R_{10}$ or at $R_{20}$ and $R_{11}$. However, the position at which a substituent is provided is not particularly limited.

In the basic skeletons represented by the general formulas [1] and [2] of this embodiment, that is, in the naphtho[2,3-e:6,7-e']diacephenanthrylene skeleton and the naphtho[2,3-e:7,6-e']diacephenanthrylene skeleton, the maximum light emission wavelength of the skeleton itself is in a blue light region.

Hence, when the position at which the substituent is provided and the type thereof are appropriately selected for this basic skeleton, a compound functioning as a blue light emitting material having a light emission peak of 460 nm or less can be provided.

The compound of this embodiment may be used as a constituent material of an organic light emitting element. In particular, when being used as a constituent material of a light emitting layer, the compound of this embodiment may be used as a dopant (guest) in the layer.

Hence, when the compound of this embodiment is used as a constituent material of the light emitting layer, an element which has a higher light emission efficiency, which maintains a high luminance for a long period of time, and which has a small degradation caused by electrical application can be obtained.

Particular examples of the fused polycyclic compound of the present invention will be shown below. However, this embodiment is not limited to those shown below.

(1) Compound 1: A compound group in which in the general formulas [1] and [2], $R_1$ to $R_{20}$ each represent a hydrogen atom or a substituent selected from a substituted or an unsubstituted alkyl group.

[Chem. 8]

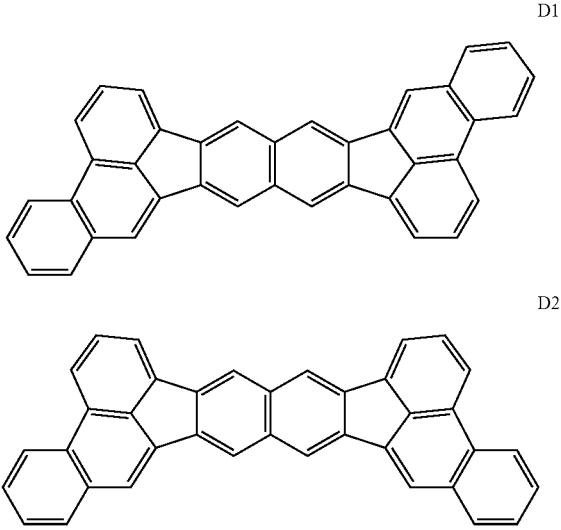

D1

D2

D3
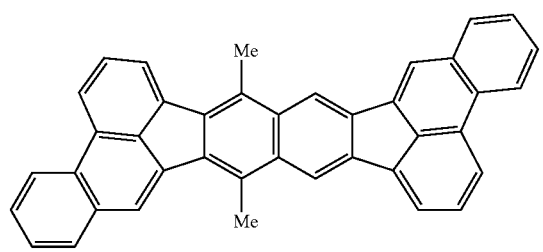
D4
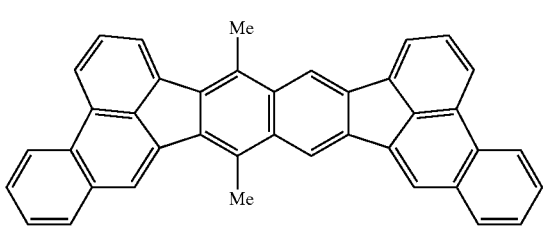
D5
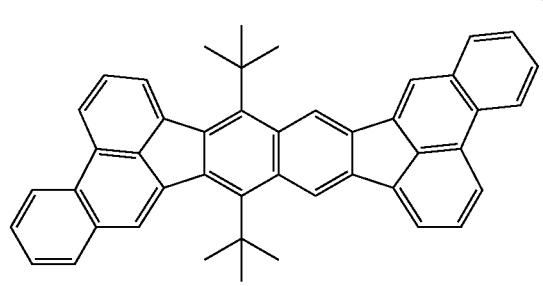
D6
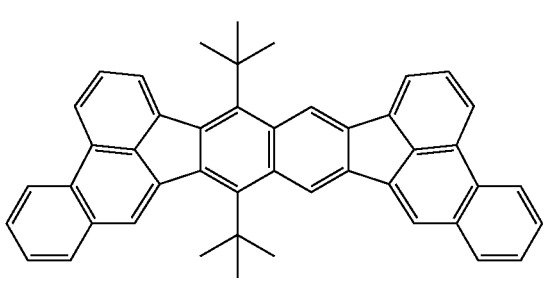 [SMILES: CC(C)(C)c1c2cc3c(cc2c(C(C)(C)C)c2c4cc5ccccc5c5cccc(c12)c54)c1cc2ccccc2c2cccc3c21]
D7
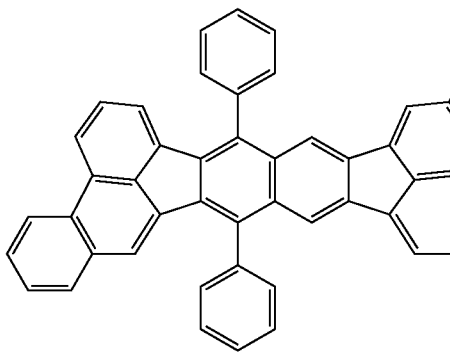
D8
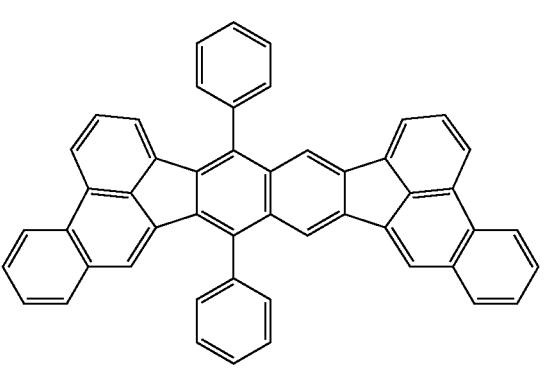 [SMILES: c1ccc(-c2c3cc4c(cc3c(-c3ccccc3)c3c5cc6ccccc6c6cccc(c23)c65)c2cc3ccccc3c3cccc4c32)cc1]
D9
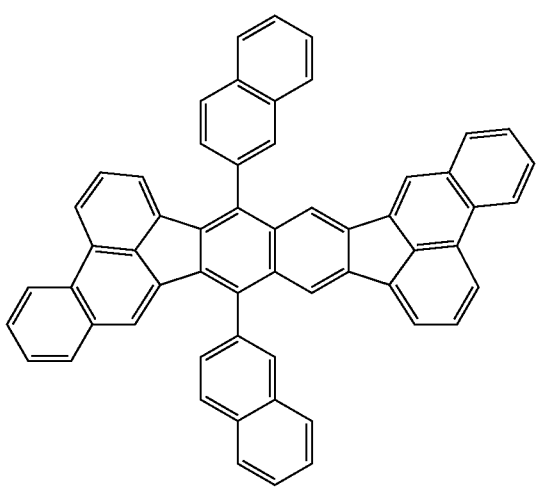
(2) Compound 2: A compound group in which in the general formulas [1] and [2], $R_1$ to $R_{20}$ each represent a hydrogen atom or a substituent selected from a substituted or an unsubstituted aryl group.

-continued
D10
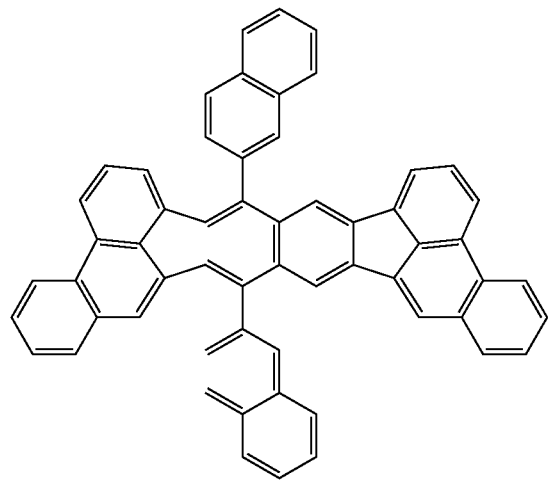
[Chem. 10]
D11
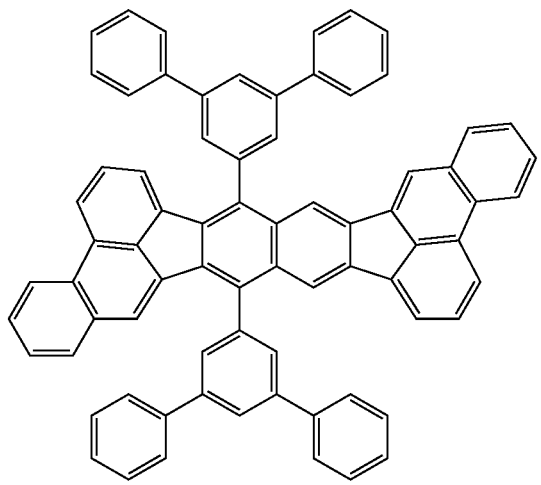
D12
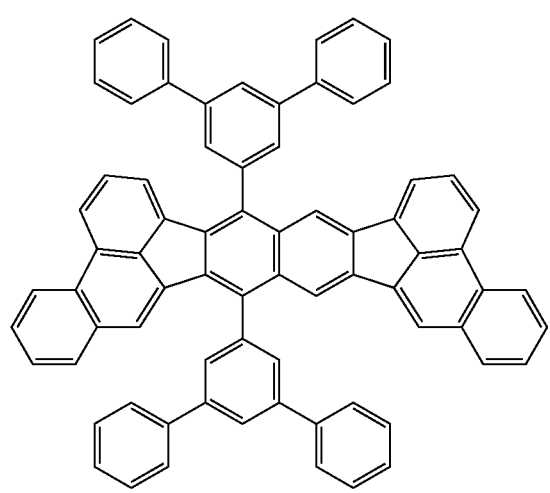
-continued
D13
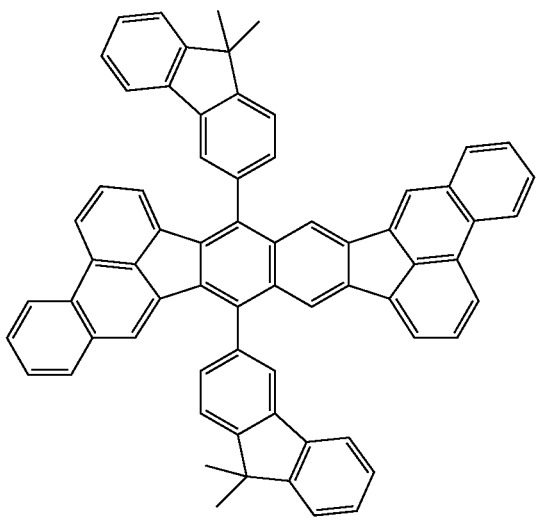
D14
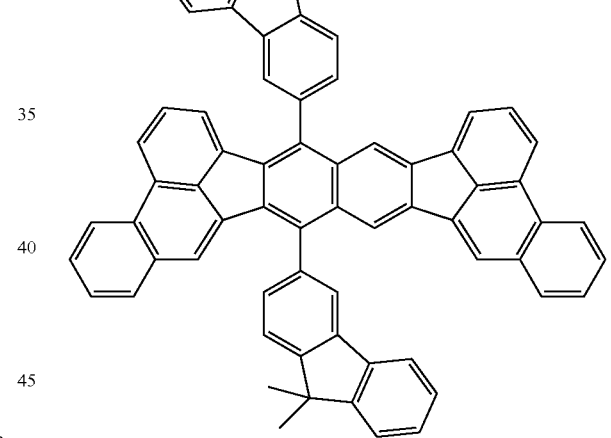
[Chem. 11]
D15
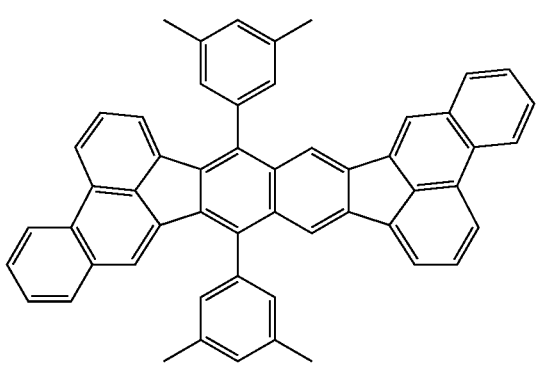

D16
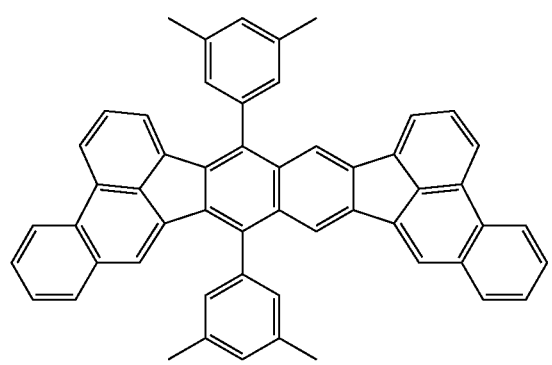
D17
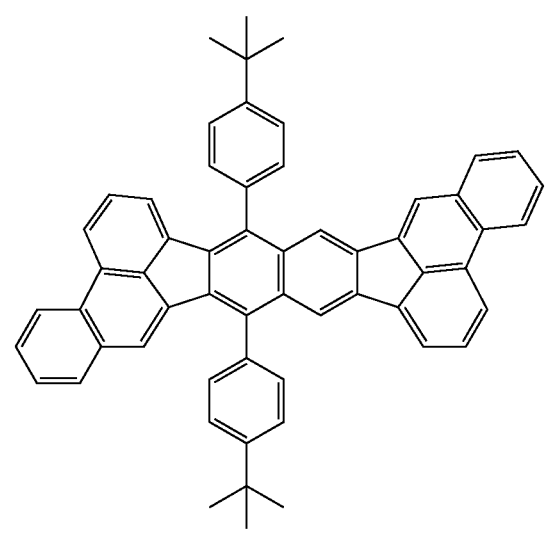
D18
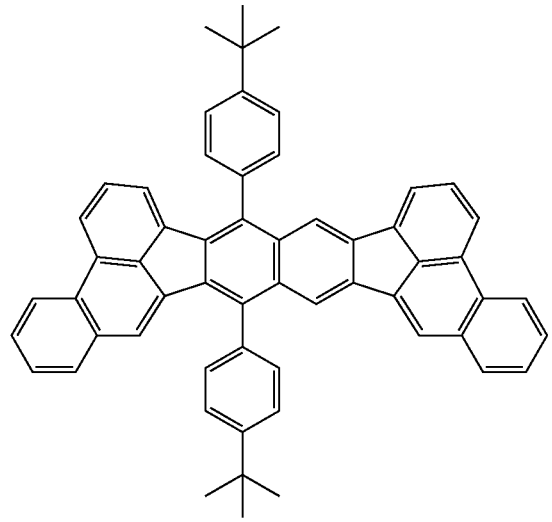
[Chem. 12]
D19
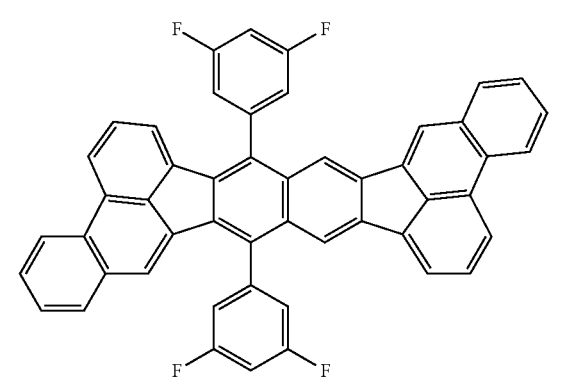
D20
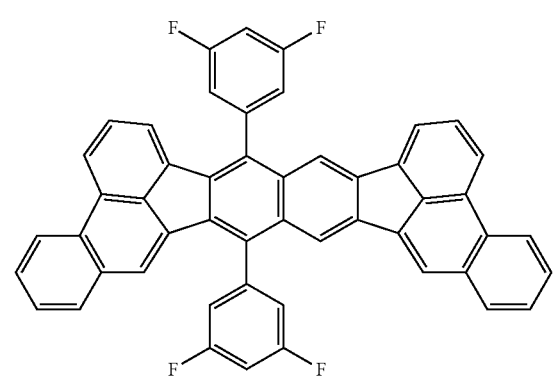
D21
D22
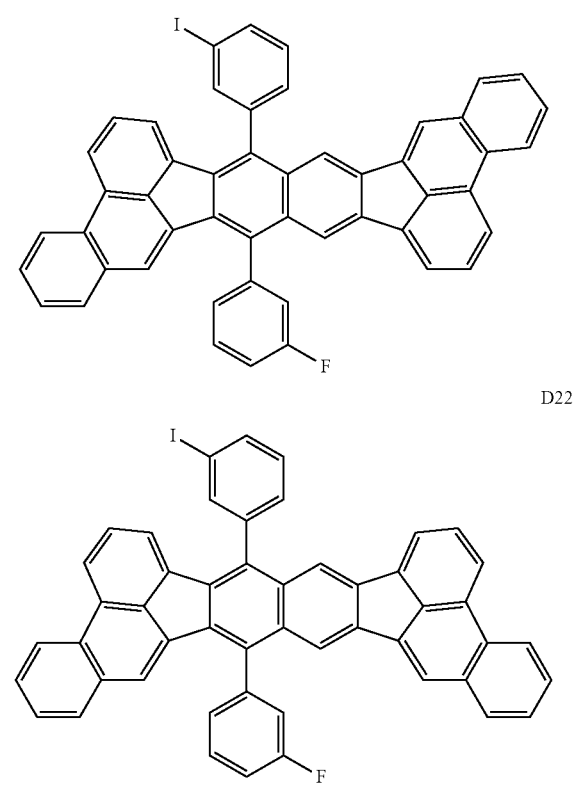

[Chem. 13]
D23
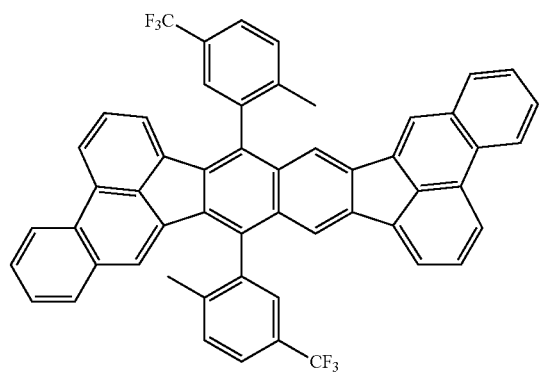
D24
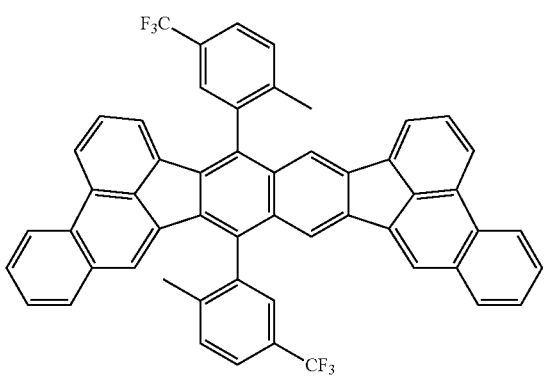
D25
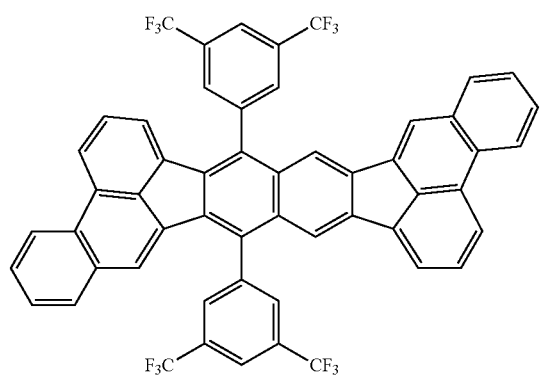
D26
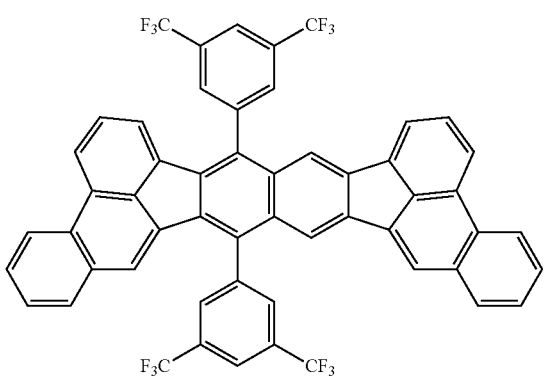
[Chem. 14]
D27
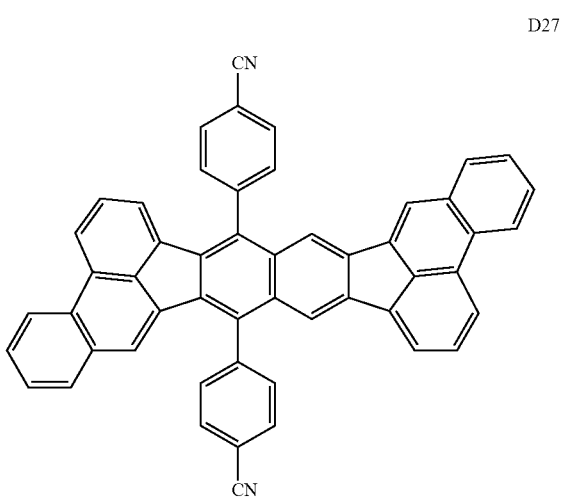
D28
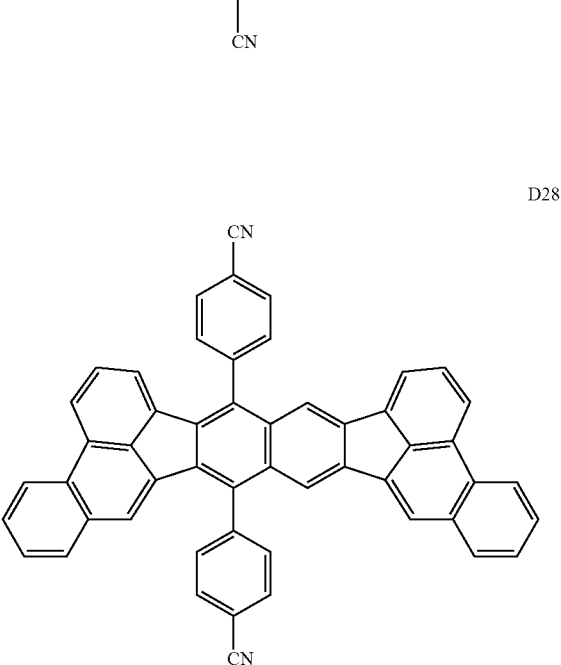
D29
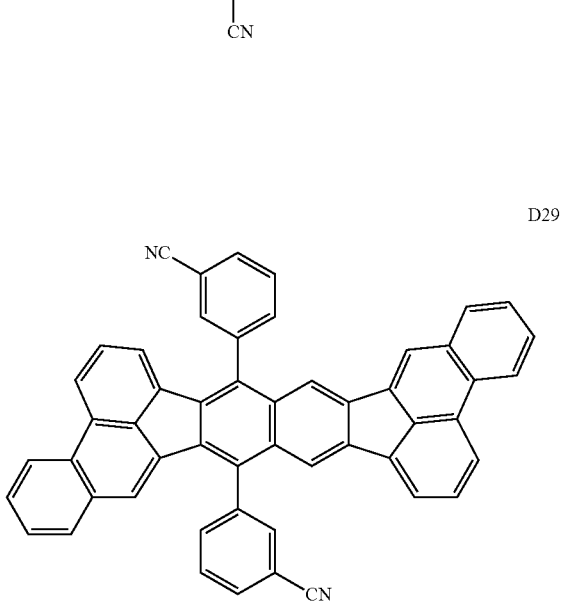

-continued
D30
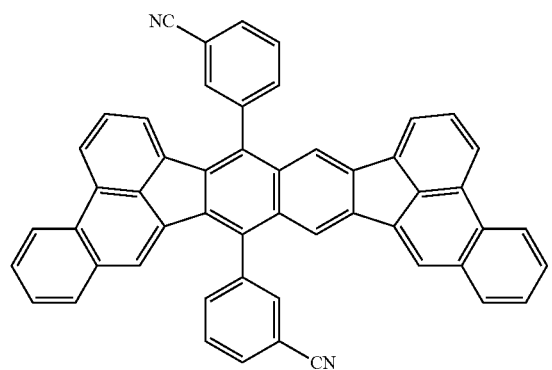
[Chem. 15]
D31
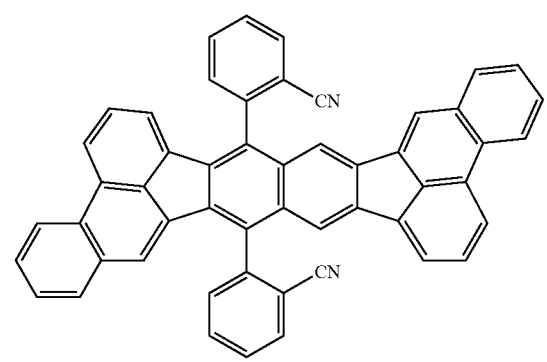
D32
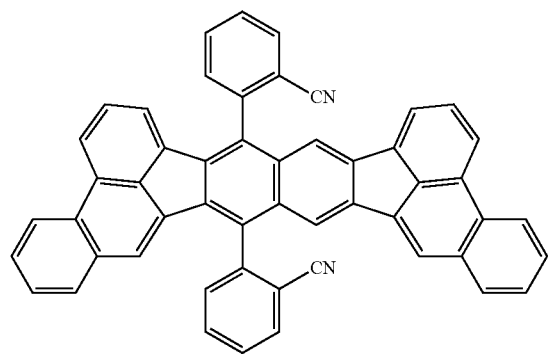
D33
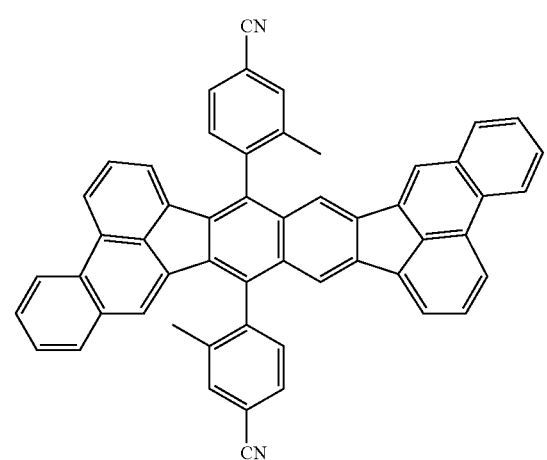
-continued
D34
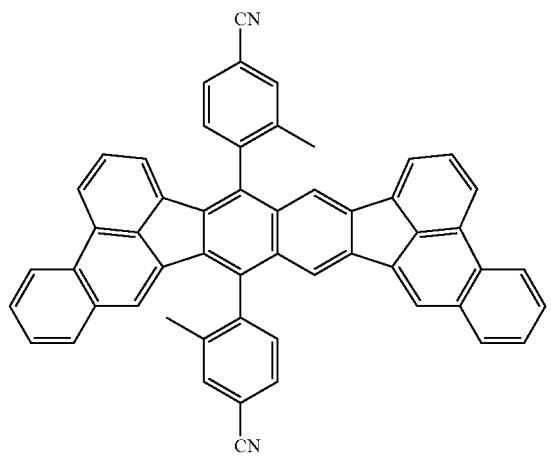
[Chem. 16]
D35
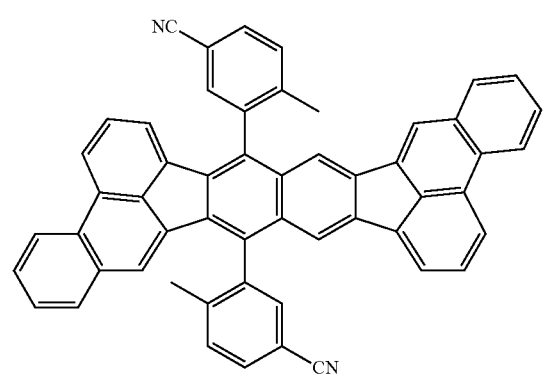
D36
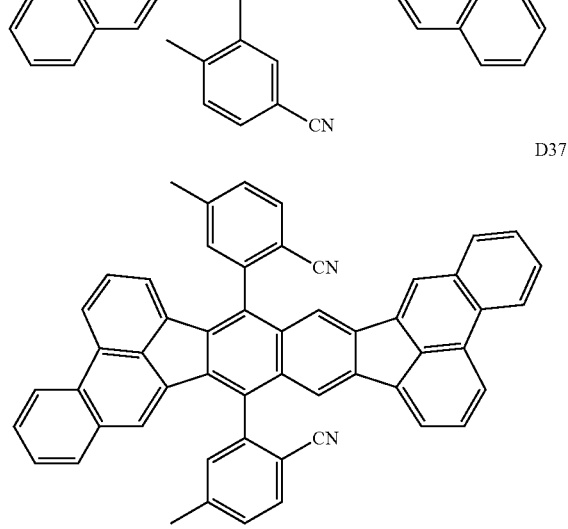
D37

D38
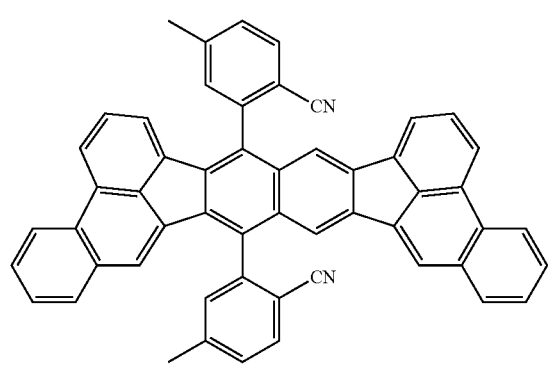
[Chem. 17]
D39
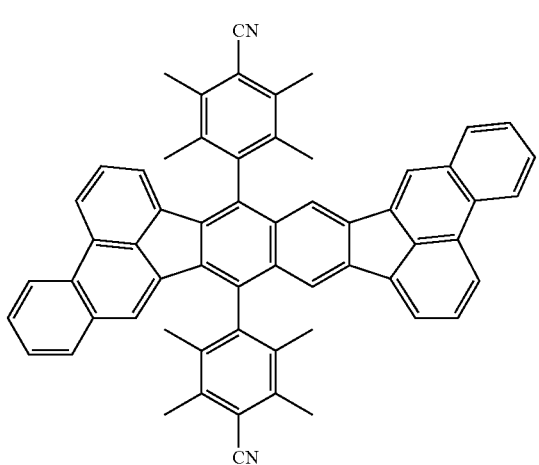
D40
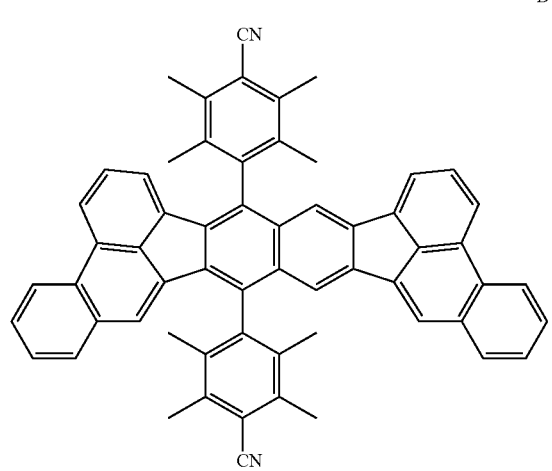
D41
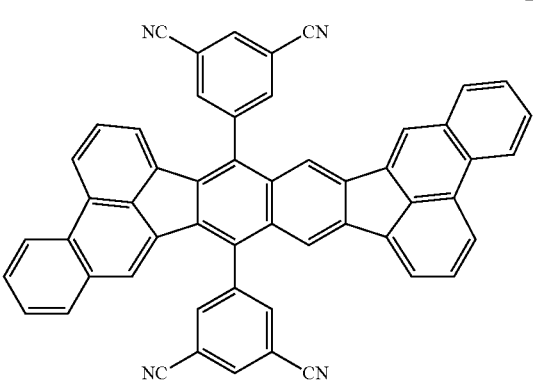
D42
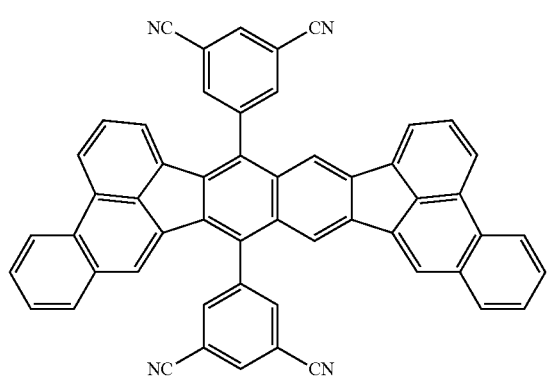
(3) Compound 3: A compound group in which in the general formulas [1] and [2], $R_1$ to $R_{20}$ each represent a hydrogen atom or a substituent selected from a substituted or an unsubstituted heterocyclic group.
[Chem. 18]
D43
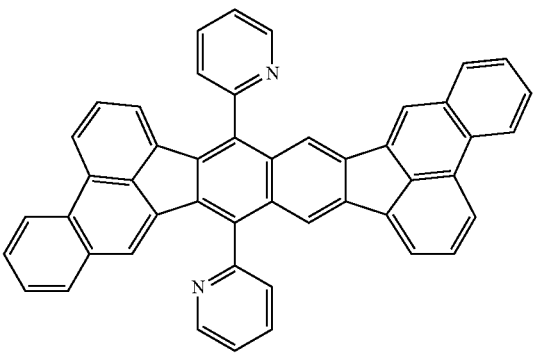

D44
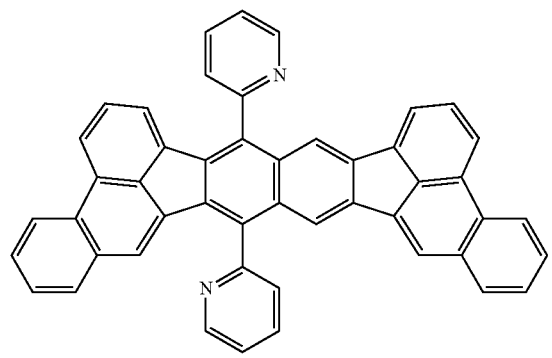
D45
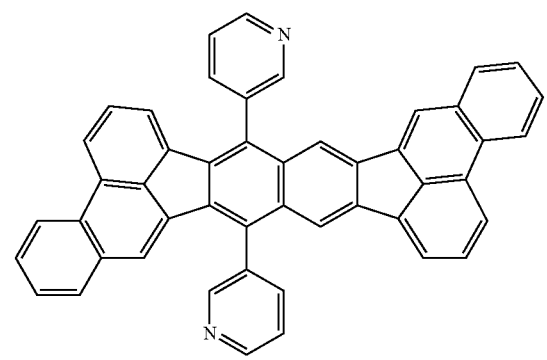
D46
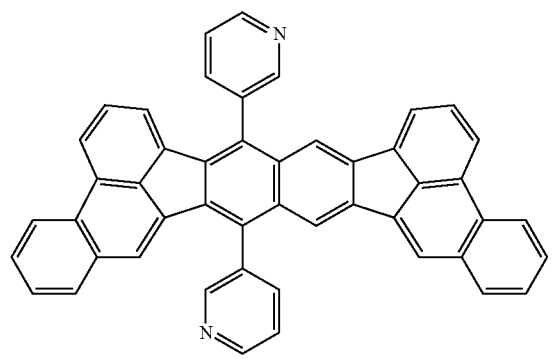
[Chem. 19]
D47
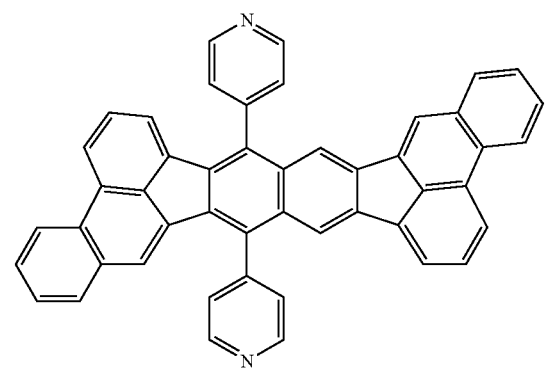
D48
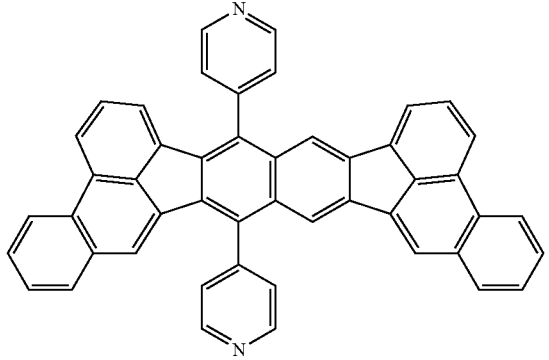
D49
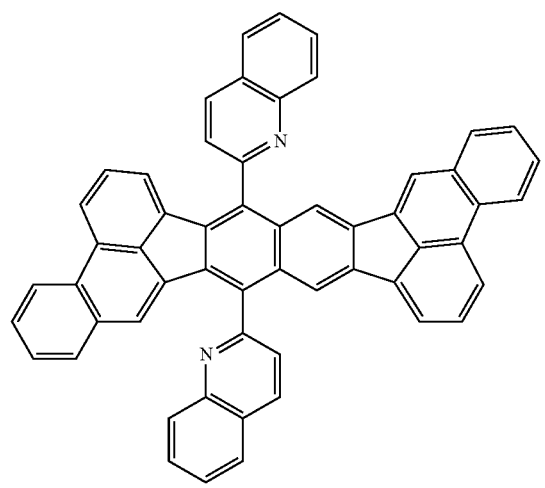
D50
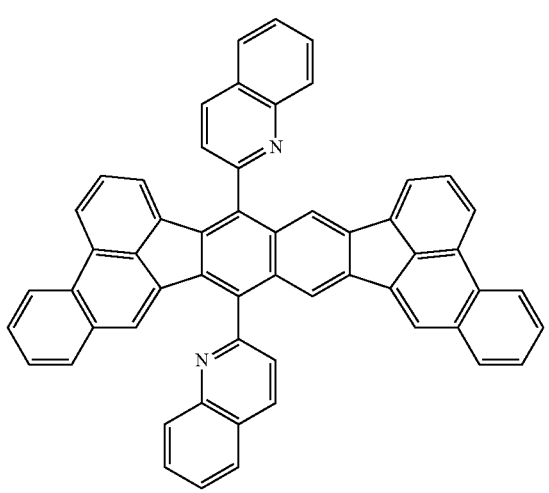

[Chem. 20]
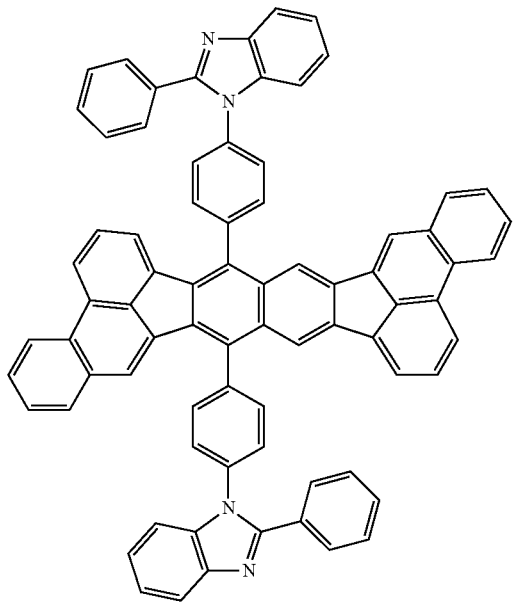
D51
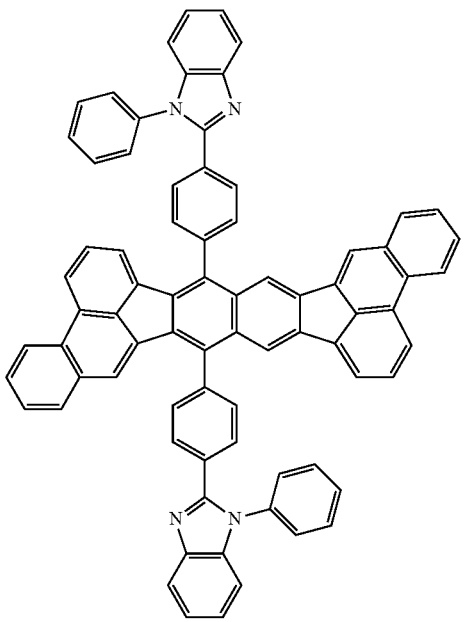
D53
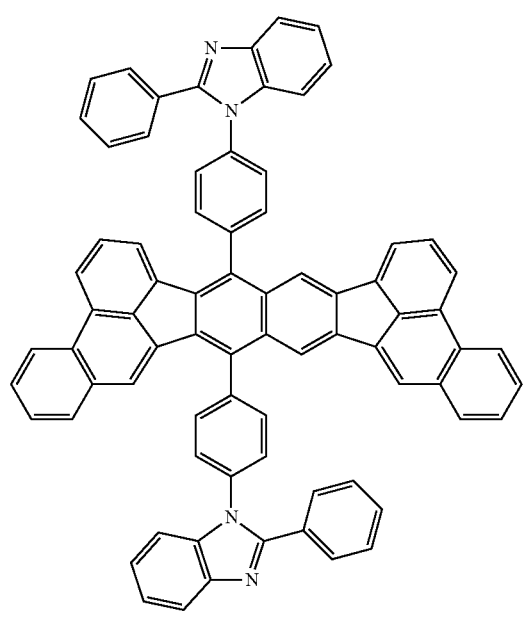
D52
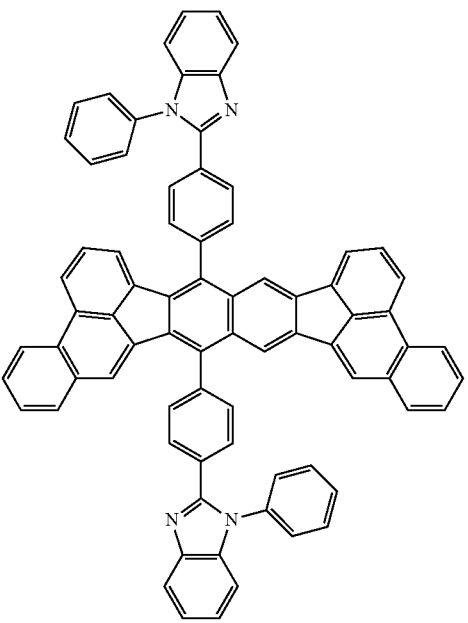
D54
Although the fused polycyclic compounds represented by the general formula [1] and [2] can be synthesized by the following synthetic routes, of course, those synthetic methods are simply shown by way of example, and the synthesis of the above fused polycyclic compounds is not limited to those synthetic methods.
Synthetic Route 1
[Chem. 21]
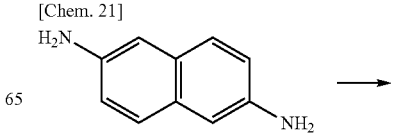

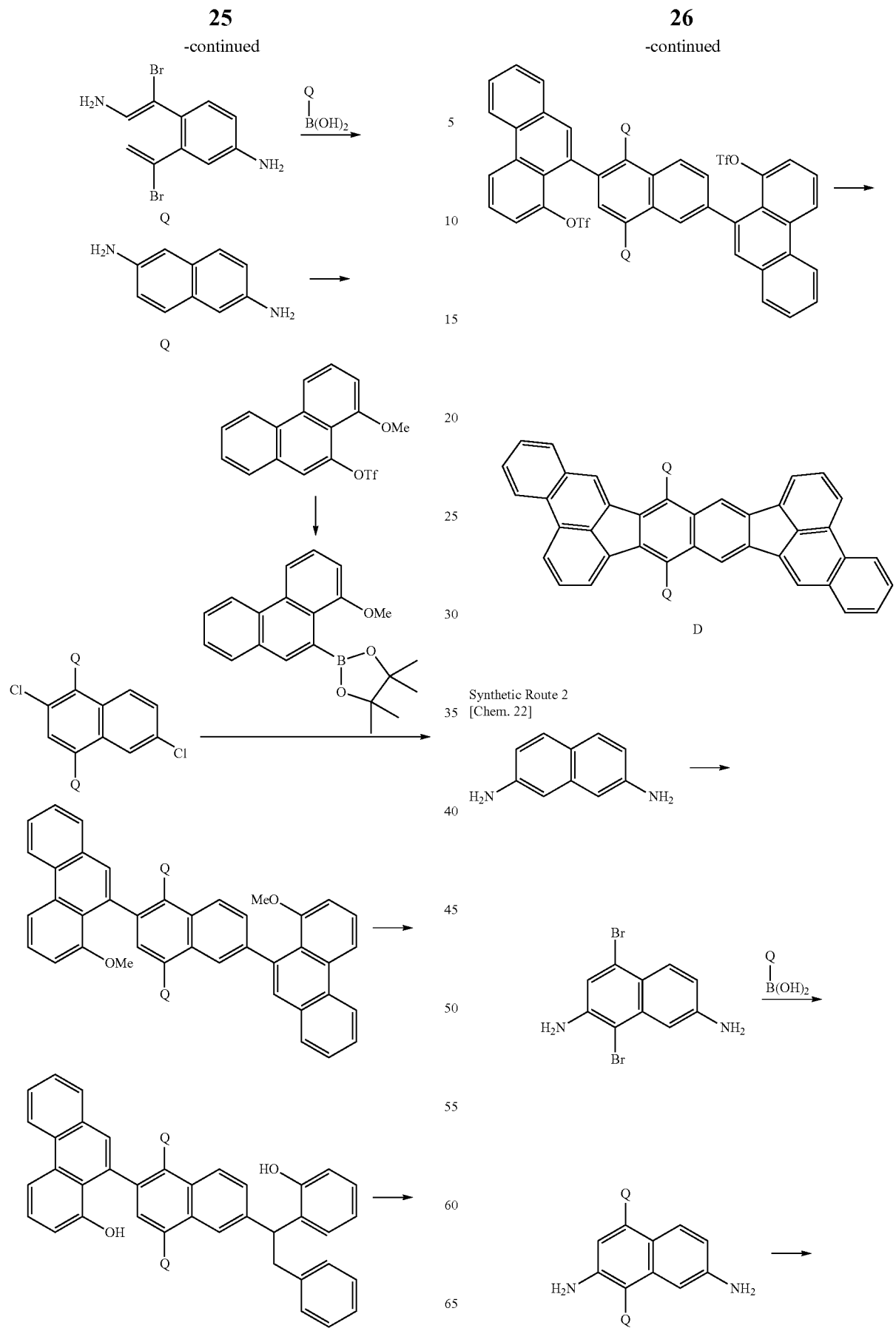

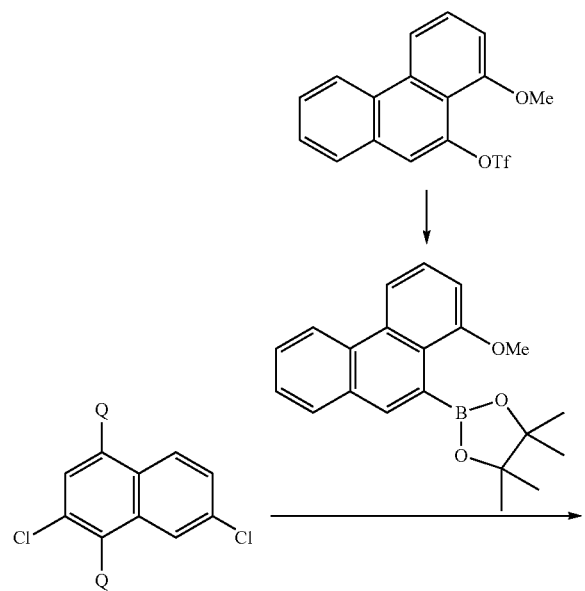
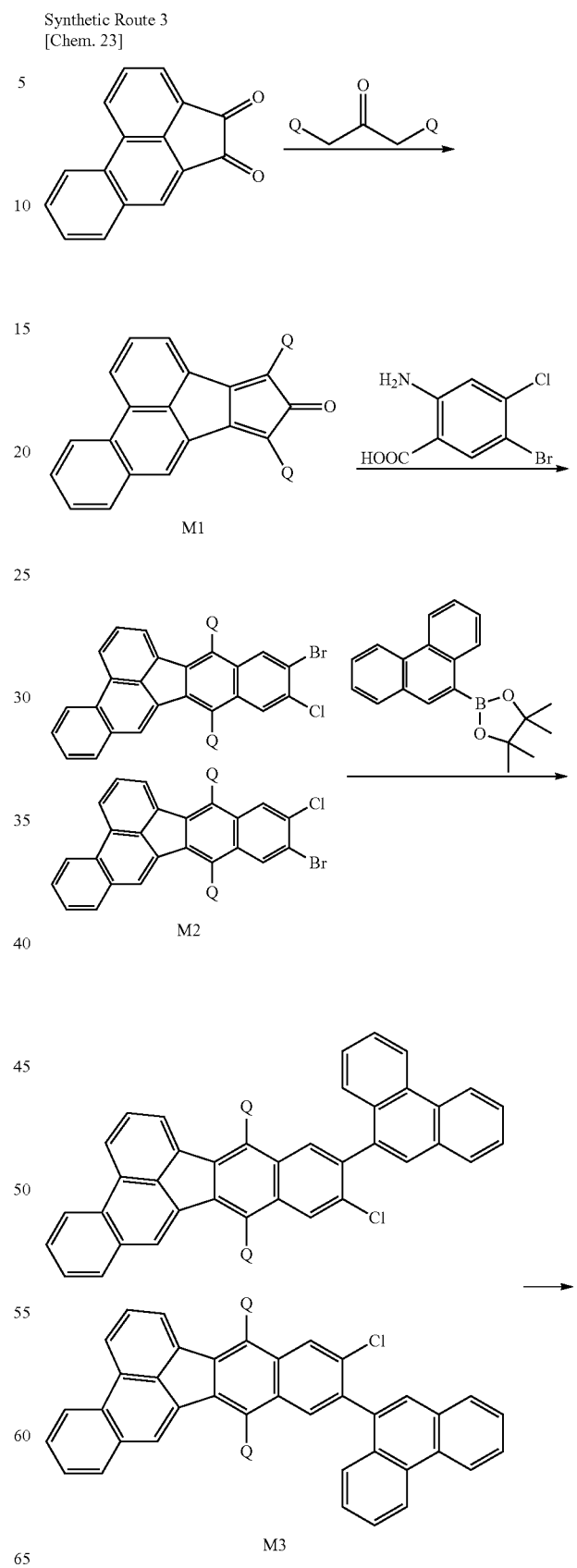
Synthetic Route 3
[Chem. 23]

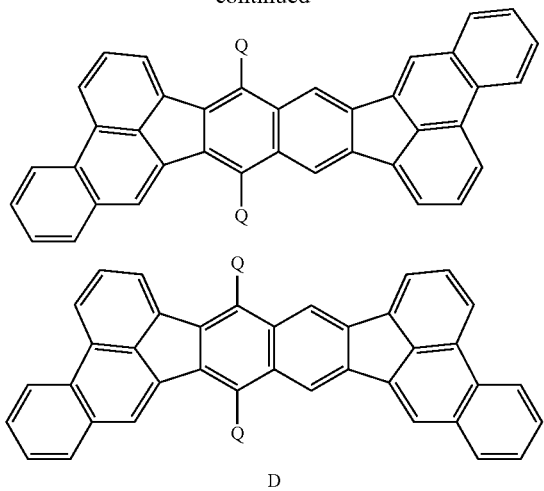

The synthetic route 1 or 2 is a method for synthesizing a single compound represented by the general formula [1] or [2], respectively. On the other hand, the synthetic route 3 is a method for synthesizing a mixture of the compounds represented by the general formulas [1] and [2].

Furthermore, Q in the synthetic routes 1 to 3 represents a substituent selected from the group consisting of a hydrogen atom, a cyano group, a substituted or an unsubstituted alkyl group, a substituted or an unsubstituted aryl group, and a substituted or an unsubstituted heterocyclic group.

Although particular examples of the substituent will be shown in Tables 2-1 and 2-2, of course, the compounds shown in Tables 2-1 and 2-2 are simply examples of the compounds of the present invention, and the compounds of the present invention are not limited to those shown in Tables 2-1 and 2-2.

In the synthetic route 3, when an intermediate M2 is synthesized in a second step, an isomer having different substituent bonding positions is also synthesized; hence, a targeted compound D is obtained in the form of a mixture containing an isomer thereof.

Since having light emission properties hardly different from those of the compound D, the isomer of the compound D may be used in combination therewith. Of course, the compound D may be isolated, for example, by recrystallization or a column chromatography, and even if the compound D is used in the form of a mixture as it is, the performance of the compound D is not particularly influenced.

When the mixture is used for an organic light emitting element, for example, an effect of suppressing concentration quenching may be expected.

Examples of the fused polycyclic compound obtained through the above synthetic route 3 are shown in Tables 2-1 and 2-2 together with the substituent Q.

TABLE 2-1

| | Q | SYNTHESIZED COMPOUND | |
|---|---|---|---|
| SYNTHETIC EXAMPLE 1 | Me— | | |
| SYNTHETIC EXAMPLE 2 | | | |
| SYNTHETIC EXAMPLE 3 | | | |

TABLE 2-1-continued
| | Q | SYNTHESIZED COMPOUND | |
|---|---|---|---|
| SYNTHETIC EXAMPLE 4 | 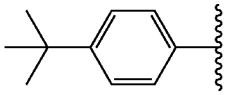 | 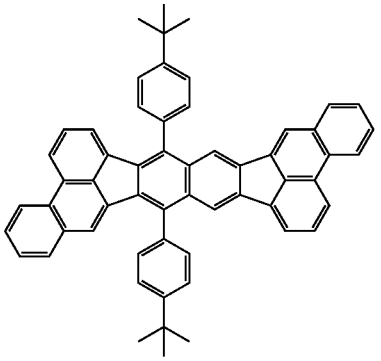 [SMILES: CC(C)(C)c1ccc(-c2c3cc4c(cc3c(-c3ccc(C(C)(C)C)cc3)c3c5cc6ccccc6c6cccc(c23)c65)c2cccc3c5ccccc5cc4c32)cc1] | 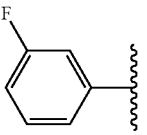 [SMILES: *c1cccc(F)c1] |
| SYNTHETIC EXAMPLE 5 | 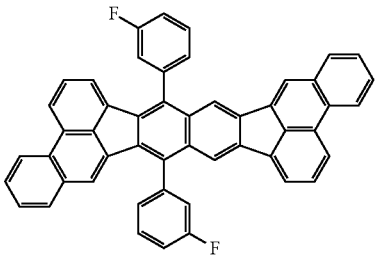 | 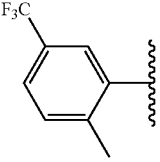 | 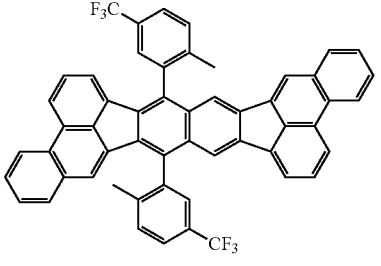 [SMILES: Cc1ccc(C(F)(F)F)cc1-c1c2cc3c(cc2c(-c2cc(C(F)(F)F)ccc2C)c2c4cc5ccccc5c5cccc(c12)c54)c1cccc2c4ccccc4cc3c21] |
| SYNTHETIC EXAMPLE 6 | 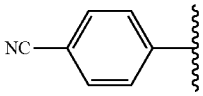 [SMILES: *c1ccc(C#N)cc1] | 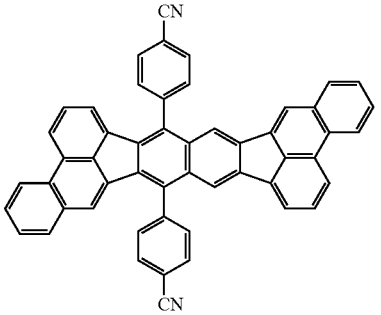 [SMILES: N#Cc1ccc(-c2c3cc4c(cc3c(-c3ccc(C#N)cc3)c3c5cc6ccccc6c6cccc(c23)c65)c2cccc3c5ccccc5cc4c32)cc1] | 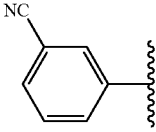 |
| SYNTHETIC EXAMPLE 7 | | | |
| SYNTHETIC EXAMPLE 8 | | | |
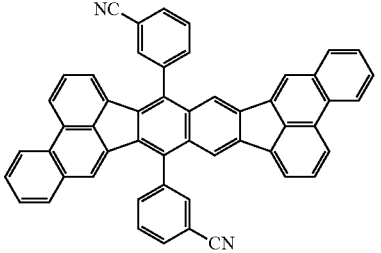 [SMILES: N#Cc1cccc(-c2c3cc4c(cc3c(-c3cccc(C#N)c3)c3c5cc6ccccc6c6cccc(c23)c65)c2cccc3c5ccccc5cc4c32)c1]

TABLE 2-1-continued

| | Q | SYNTHESIZED COMPOUND | |
|---|---|---|---|
| SYNTHETIC EXAMPLE 9 | (2-cyanophenyl) | (structure) | (structure) |
| SYNTHETIC EXAMPLE 10 | (4-cyano-2-methylphenyl) | (structure) | (structure) |
| SYNTHETIC EXAMPLE 11 | (3,5-dicyanophenyl) | (structure) | (structure) |

TABLE 2-2

| | Q | SYNTHESIZED COMPOUND | |
|---|---|---|---|
| SYNTHETIC EXAMPLE 12 | (2-pyridyl) | (structure) | (structure) |
| SYNTHETIC EXAMPLE 13 | (3-pyridyl) | (structure) | (structure) |

TABLE 2-2-continued

| Q | SYNTHESIZED COMPOUND |
|---|---|
| SYNTHETIC EXAMPLE 14 | 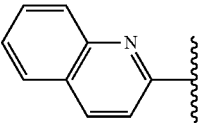 |
| SYNTHETIC EXAMPLE 15 | 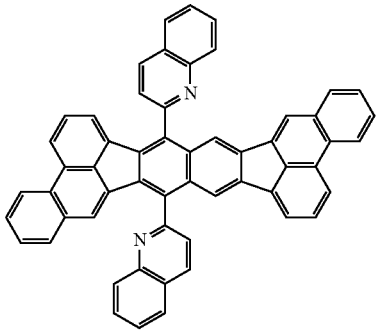 [SMILES: c1ccc2nc(-c3c4cc5c(cc4c(-c4ccc6ccccc6n4)c4c6cc7ccccc7c7cccc(c34)c76)c3cccc4c6ccccc6cc5c43)ccc2c1] |

[2] Organic Light Emitting Element of this Embodiment

Next, an organic light emitting element of this embodiment will be described.

The organic light emitting element of this embodiment includes a pair of electrodes, that is, an anode and a cathode, and at least one organic compound layer disposed between the anode and the cathode. This organic compound layer contains the fused polycyclic compound represented by the general formula [1] or [2].

The organic compound layer of the organic light emitting element of this embodiment is a single layer or a laminate including a plurality of layers, the single layer and the laminate each containing at least one light emitting layer.

When the organic compound layer is a laminate including a plurality of layers, the organic compound layer includes, besides the light emitting layer, at least one of a hole injection layer, a hole transport layer, an electron transport layer, an electron injection layer, a hole-exciton block layer, and the like.

In the organic light emitting element of this embodiment, the fused polycyclic compound of the present invention may be contained in any layer forming the organic light emitting element. In particular, for example, the hole injection layer, the hole transport layer, the light emitting layer, the hole-exciton block layer, and the electron transport layer may be mentioned. Among those mentioned above, the fused polycyclic compound of the present invention is more preferably contained in the light emitting layer.

Hereinafter, particular examples of the organic light emitting element of this embodiment are shown below.

(i) (anode/)light emitting layer(/cathode)
(ii) (anode/)hole transport layer/light emitting layer/electron transport layer(/cathode)
(iii) (anode/)hole transport layer/light emitting layer/hole-exciton block layer/electron transport layer(/cathode)
(iv) (anode/)hole injection layer/hole transport layer/light emitting layer/electron transport layer(/cathode)
(v) (anode/)hole transport layer/light emitting layer/hole-exciton block layer/electron transport layer/electron injection layer(/cathode)
(vi) (anode/)hole injection layer/hole transport layer/light emitting layer/hole-exciton block layer/electron transport layer(/cathode)
(vii) (anode/)hole injection layer/hole transport layer/light emitting layer/electron transport layer/electron injection layer(/cathode)

However, the structures of the above (i) to (vii) are each merely shown as a particular example of the basic element structure, and the structure of the organic compound layer of the organic light emitting element of this embodiment is not limited to those described above.

Furthermore, when the fused polycyclic compound of this embodiment is contained in the light emitting layer, the light emitting layer may be formed only from at least one of naphtho[2,3-e:6,7-e′]diacephenanthrylene and naphtho[2,3-e:7,6-e′]diacephenanthrylene represented by the general formulas [1] and [2], respectively, which are the fused polycyclic compounds of this embodiment, or may be formed of a host and a guest.

When the light emitting layer is formed of a host and a guest, the fused polycyclic compound of the present invention is preferably used as the guest.

In addition, when the fused polycyclic compound of the present invention is used as the guest, the concentration of the guest to the host is preferably 0.1 to 30 percent by weigh and more preferably 0.5 to 10 percent by weight.

In this embodiment, the host is a compound having the highest weight ratio among compounds forming the light emitting layer, and the guest is a compound which has a weight ratio lower than that of the host among the compounds forming the light emitting layer and which is responsible for primary light emission. The guest is also called a dopant in some cases.

The light emitting layer of the organic light emitting element of this embodiment may further contain an assist. The assist is a compound which has a weight ratio lower than that of the host among the compounds forming the light emitting layer and which assists light emission of the guest. The assist is also called a second host in some cases.

Besides the fused polycyclic compound of the present invention, the organic light emitting element of this embodiment may also use at least one of known low molecular weight and high molecular weight materials if necessary.

In particular, the above material may be used as a constituent material, such as a hole injection material, a hole transport material, a host, an electron transport material, or an electron injection material.

Hereinafter, particular examples of those materials will be mentioned.

AS the hole injection material or the hole transport material, a material having a high hole mobility is preferably used. As a low molecular weight and a high molecular weight material having a hole injection ability or a hole transport ability, although a triarylamine derivative, a phenylenediamine derivative, a stilbene derivative, a phthalocyanine derivative, a porphyrin derivative, a poly(vinyl carbazole), a polythiophene, and other conductive polymers may be mentioned by way of example, of course, the material is not limited to those mentioned above.

As the host, although a triarylamine derivative, a phenylene derivative, a fused ring aromatic compound (such as a naphthalene derivative, a phenanthrene derivative, a fluorene derivative, a chrysene derivative, an anthracene derivative, or a pyrene derivative), an organic metal complex (an organic aluminum complex, such as tris(8-quinolinolato) aluminum, an organic beryllium complex, an organic iridium complex, an organic platinum complex, or the like), and a polymer derivative, such as a poly(phenylene vinylene) derivative, a polyfluorene derivative, a polyphenylene derivative, a poly(thienylene vinylene) derivative, or a polyacetylene derivative, may be mentioned by way of example, of course, the host is not limited to those mentioned above.

The electron injection material or the electron transport material is selected in consideration, for example, of the balance with the hole mobility of the hole injection material or the hole transport material.

As a material having an electron injection ability or an electron transport ability, although an oxadiazole derivative, an oxazole derivative, a pyrazine derivative, a triazole derivative, a triazine derivative, a quinoline derivative, a quinoxaline derivative, a phenanthroline derivative, and an organic aluminum complex may be mentioned by way of example, of course, the material is not limited to those mentioned above.

Next, constituent materials of the organic light emitting element other than the organic compound layer will be described.

As a constituent material of the anode, a material having a higher work function is more preferable. For example, there may be mentioned a metal element, such as gold, platinum, silver, copper, nickel, palladium, cobalt, selenium, vanadium, or tungsten; an alloy containing at least two of those metal elements in combination; or a metal oxide, such as titanium oxide, zinc oxide, indium oxide, indium titanium oxide (ITO), or indium zinc oxide.

In addition, a conductive polymer, such as a polyaniline, a polypyrrole, or a polythiophene, may also be used. Those electrode materials may be used alone, or at least two types thereof may be used in combination. In addition, the anode may have either a single layer structure or a multilayer structure.

On the other hand, as a constituent material of the cathode, a material having a low work function is preferable. For example, an alkali metal, such as lithium; an alkaline earth metal, such as calcium; and a metal element, such as aluminum, titanium, manganese, silver, lead, or chromium, may be mentioned. Alternatively, an alloy containing at least two of the above metal elements in combination may also be used.

As an alloy containing metal elements in combination, for example, there may be mentioned magnesium-silver, aluminum-lithium, or aluminum-magnesium. In addition, a metal oxide, such as indium titanium oxide (ITO), may also be used.

Those electrode materials may be used alone, or at least two types thereof may be used in combination. In addition, the cathode may have either a single layer structure or a multilayer structure.

The organic compound layer of the organic light emitting element of this embodiment may be formed, for example, by a vacuum deposition method, an ionization deposition method, a sputtering method, a plasma deposition method, or a coating method.

The coating method is a method for applying a material dissolved in an appropriate solvent, and for example, a spin coating method, a dipping method, a casting method, an LB method, or an ink jet method may be mentioned.

When a layer is formed by a vacuum deposition method or a solution coating method, for example, crystallization is not likely to occur, and an excellent aging stability can be obtained. In addition, when a coating method is used, a film may be formed in combination with an appropriate binder resin.

As the above binder resin, although a poly(vinyl carbazole) resin, a polycarbonate resin, a polyester resin, an ABS resin, an acrylate resin, a polyimide resin, a phenol resin, an epoxy resin, a silicone resin, and a urea resin may be mentioned by way of example, the binder resin is not limited to those mentioned above.

In addition, those binder resins mentioned above may be used alone as a homopolymer or a copolymer, or at least two types thereof may be used in combination. Furthermore, if necessary, additives, such as a known plasticizer, antioxidant, and UV absorber, may also be used.

[3] Application of Organic Light Emitting Element

The organic light emitting element of this embodiment may be used as a structural member of a display device or a lighting device. Besides those mentioned above, the organic light emitting element may also be used, for example, as an exposure light source of an electrophotographic image forming device, a backlight of a liquid crystal display device, or a light source of lighting. The organic light emitting element may further have a color filter.

A display device of this embodiment has the organic light emitting element of this embodiment in a display portion including a plurality of pixels.

In addition, this pixel has the organic light emitting element of this embodiment and an active element. As one example of the active element, a switching element controlling light emission luminance may be mentioned, and as one example of the switching element, a TFT element may be mentioned.

An anode or a cathode of this organic light emitting element is connected to a drain electrode or a source electrode of a TFT element. The display device may be used as an image display device of a personal computer (PC). The TFT element is provided on an insulating surface of a substrate.

The display device may be an image information processing device having an input portion to which image information is input from an area CCD, a linear CCD, and/or a memory card and a display portion which displays an input image.

In addition, a display portion of the image information processing device or the image forming device may have a touch panel function. In addition, the display device may be used for a display portion of a multifunctional printer.

A lighting device is a device lighting the inside of a room. The lighting device may also be a device emitting light having a wavelength of white, natural white, blue, red, or the like.

When emitting white light, the organic light emitting element of this embodiment preferably contains at least two types of light emitting materials. When at least two types of light emitting materials are contained, a plurality of light emitting layers may be formed, or a light emitting layer may contain at least two types of light emitting materials.

When a plurality of light emitting layers is formed, the light emitting layers may be laminated to each other or disposed side by side. The side-by-side disposition described above indicates an arrangement in which the light emitting layers are respectively disposed in contact with an adjacent layer located at an anode side and an adjacent layer located at a cathode side.

A lighting device of this embodiment includes the organic light emitting element of this embodiment and an AC/DC converter circuit which is connected thereto and which supplies a drive voltage. The lighting device may also have a color filter.

In the AC/DC converter circuit of this embodiment is a circuit converting an alternating current voltage to a direct current voltage.

An image forming device of this embodiment is an image forming device including a photoreceptor, a charging portion charging the surface of this photoreceptor, an exposure portion exposing the photoreceptor to form an electrostatic latent image, and a developer developing the electrostatic latent image formed on the surface of the photoreceptor, and the exposure portion has the organic light emitting element of this embodiment.

As the exposure portion, for example, an exposure device having the organic light emitting elements of this embodiment may be mentioned. The organic light emitting elements of the exposure device may be arranged along a long axis direction of the photoreceptor to form lines or may be arranged so that light is emitted from the entire exposing surface of the exposure device.

Next, a display device using the organic light emitting element of this embodiment will be described with reference to FIG. 1.

FIG. 1 is a schematic cross-sectional view of a display device including the organic light emitting element of this embodiment and a TFT element which is one example of a switching element and which is connected to the organic light emitting element. FIG. 1 shows two sets each including the organic light emitting element and the TFT element. Hereinafter, the details of the structure will be described.

This display device includes a substrate 1, such as a glass, and a moisture proof film 2 provided thereon to protect a TFT element or an organic compound layer. In addition, reference numeral 3 indicates a metal gate electrode, reference numeral 4 indicates a gate insulating film, and reference numeral 5 indicates a semiconductor layer.

A TFT element 8 has the semiconductor layer 5, a drain electrode 6, and a source electrode 7. An insulating film 9 is provided on the TFT element 8. An anode 11 of the organic light emitting element is connected to the source electrode 7 through a contact hole 10 interposed therebetween. The display device is not limited to the structure described above, and one of the anode and the cathode may be connected to one of the source electrode and the drain electrode of the TFT element.

Although an organic compound layer 12 may be a laminate formed of organic compound layers, in FIG. 1, multiple organic compound layers are shown as if only one layer is present. A first protective layer 14 and a second protective layer 15 are provided on a cathode 13 to suppress degradation of the organic light emitting element.

In the display device of this embodiment, an MIM element may also be used as a switching element instead of using the transistor.

The active element of the organic light emitting element of this embodiment may be directly formed in the substrate, such as a Si substrate. The "directly formed in the substrate" indicates that a transistor is formed by processing the substrate itself, such as a Si substrate.

The structure is selected in accordance with the definition, and for example, when the definition is approximately QVGA per inch, the active element is preferably directly formed in a Si substrate. The active element directly formed in a substrate is preferably a transistor.

When the display device using the organic light emitting element of this embodiment is driven, a stable display having a superior image quality can be performed for a long time.

EXAMPLES

Hereinafter, this embodiment will be described in detail with reference to examples. However, this embodiment is not limited thereto.

Example 1

Synthesis of Example Compounds D27 and D28

In accordance with the method described below, example compounds D27 and D28 were synthesized. For this synthesis, the synthetic route 3 was used.

Synthetic Route 3
[Chem. 24]
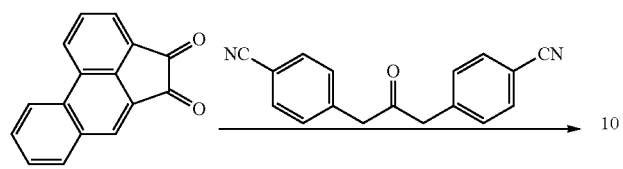
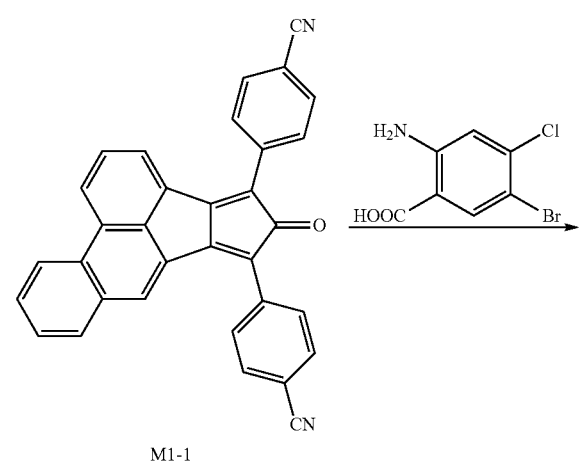
M1-1
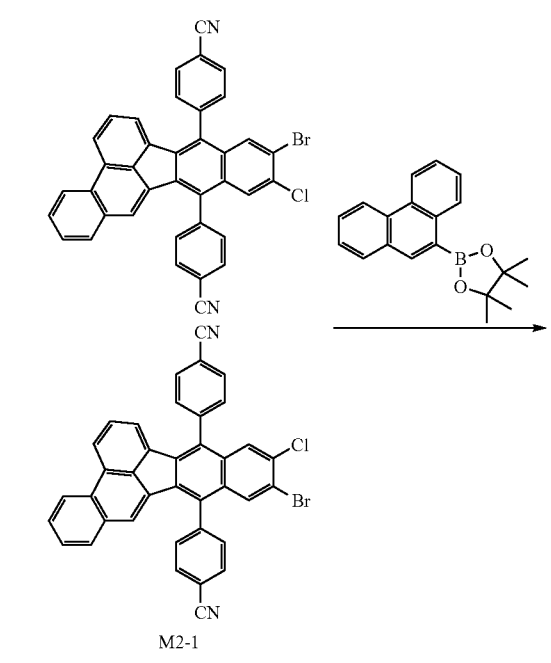
M2-1
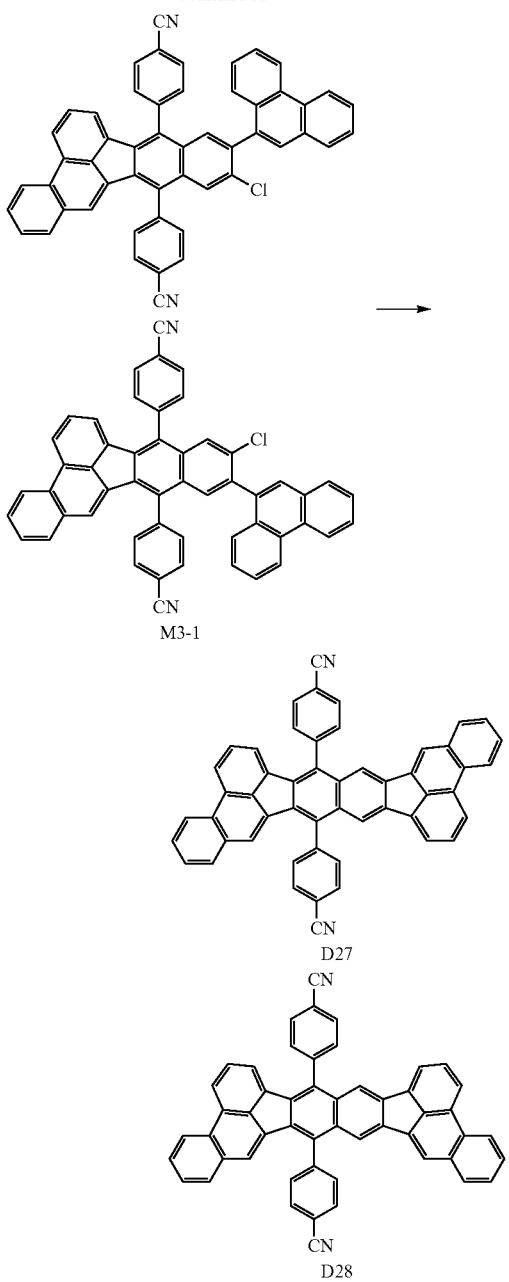
M3-1
D27
D28
(1) Synthesis of Intermediate M1-1
[Chem. 25]
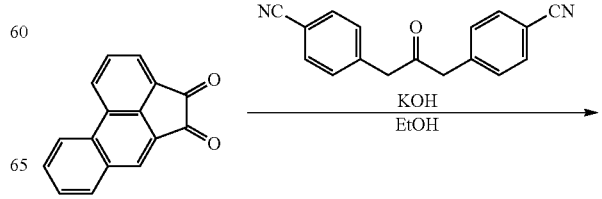

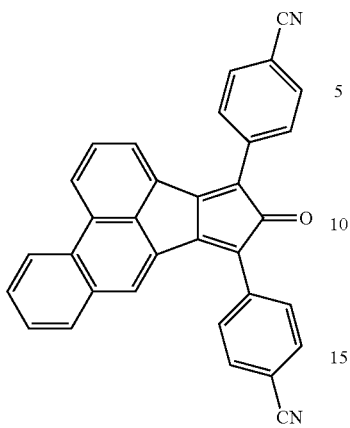

Into a four-neck flask having a volume of 500 ml in an argon atmosphere, acephenanthrylene-4,5-dione (5.30 g, 22.8 mmol), 4,4'-(2-oxopropane-1,3-diyl)dibenzonitrile (7.13 g, 27.4 mmol), and 90 ml of ethanol were charged and then stirred at room temperature.

An ethanol solution containing 0.5 M potassium hydroxide in an amount of 137 ml was dripped over 5 minutes to the mixture described above, and after heated and stirred at 50° C. for 2 hours, the mixture was spontaneously cooled to 30° C. After a powder recovered by filtration was sequentially dispersed in and washed with 100 ml of ethanol and 100 ml of toluene in this order, filtration was performed, and drying was then performed at 80° C. under a reduced pressure, so that 3.49 g (yield: 33.5%) of a black crystal was obtained.

(2) Synthesis of Intermediate M2-1

[Chem. 26]

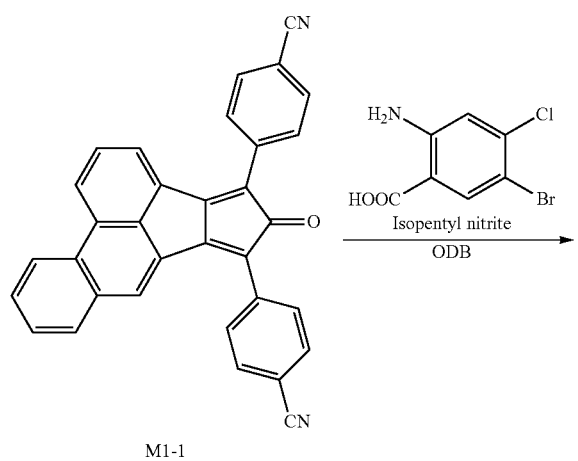

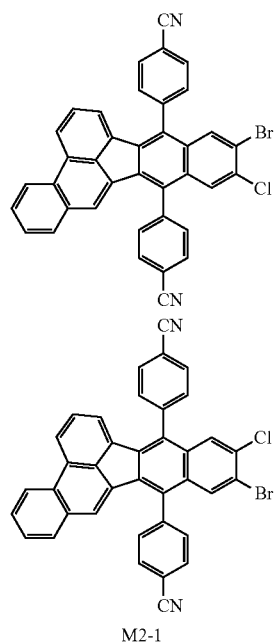

M2-1

Into a four-neck flask having a volume of 20 L in an argon atmosphere, 5.56 g (12.2 mmol) of the intermediate M1-1 and 12.2 L of 1,2-dichlorobenzene were charged and then stirred at 90° C., and the dissolution thereof was confirmed.

After 11.52 g (98.3 mmol) of isopentyl nitrite and 11.46 g (45.7 mmol) of 2-amino-5-bromo-4-chlorobenzene carboxylic acid were charged into a four-neck flask, the mixture thus prepared was heated and stirred at 90° C. for 1 hour, so that the mixture was changed into an orange-colored solution.

After spontaneous cooling was performed to room temperature, the solution thus obtained was allowed to pass through 500 g of silica gel, and the filtrate obtained therefrom was concentrated. Subsequently, recrystallization was performed using heptane, and the crystal thus obtained was dried at 80° C. under a reduced pressure, so that 3.56 g (yield: 47.3%) of a pale yellow crystal was obtained.

(3) Synthesis of Intermediate M3-1

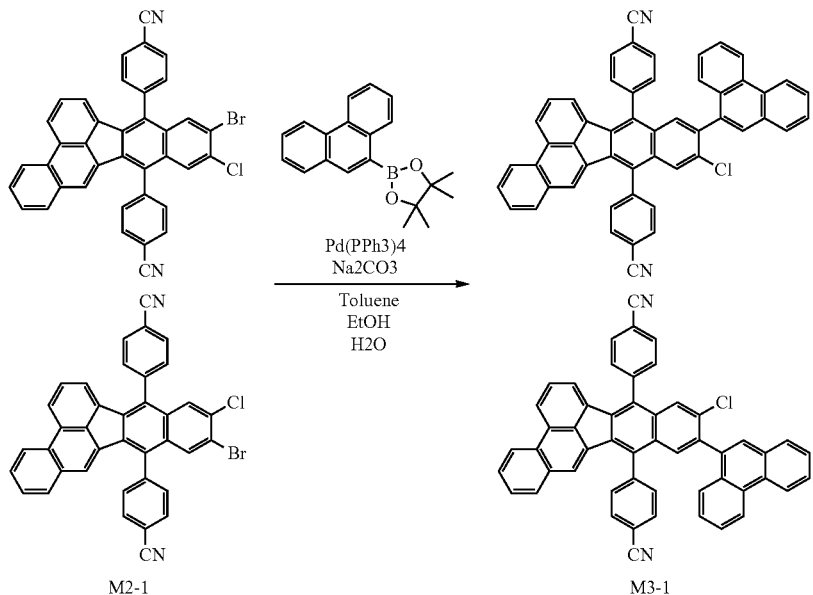

Into a four-neck flask having a volume of 300 ml in an argon atmosphere, 4.50 g (7.28 mmol) of the intermediate M2-1, 3.42 g (11.2 mmol) of (4,4,5,5-tetramethyl-1,3,2-dioxaborolane-2-yl)phenanthrene, 2.38 g (22.5 mmol) of sodium carbonate, 90 ml of toluene, 7 ml of purified water, and 0.66 g (0.57 mmol) of tetrakis(triphenylphosphine) palladium(0) were charged, and heat refluxing was then performed for 7 hours.

After spontaneous cooling was performed to room temperature, a precipitated crystal was recovered by filtration and was then dispersed in and washed with 30 ml of methanol. After spontaneous cooling was performed, a brown crystal obtained by filtration was purified using a silica gel chromatography, so that 2.60 g (yield: 49.9%) of a yellow crystal was obtained.

(4) Synthesis of Example Compound D27 and D28

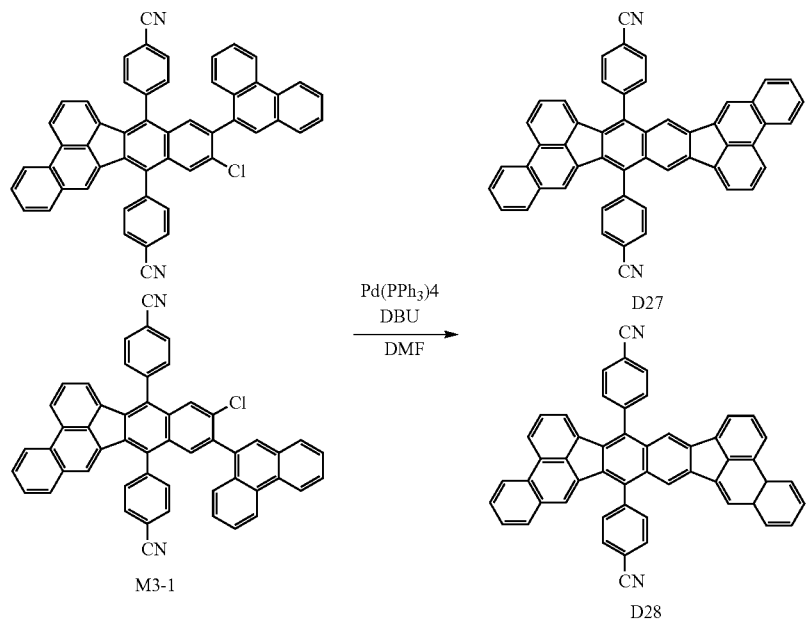

Into a four-neck flask having a volume of 200 ml in an argon atmosphere, 2.6 g (3.64 mmol) of the intermediate M3-1, 75 ml of N,N-dimethylformamide, 1.68 g (11.0 mmol) of diazabicycloundecene, and 0.86 g (0.74 mmol) of tetrakis(triphenylphosphine)palladium(0) were charged, and heat refluxing was then performed at 120° C. to 140° C. for 5 hours.

After spontaneous cooling was performed to room temperature, 150 ml of purified water was added, and a yellow crystal was obtained by filtration. After the crystal thus obtained was dissolved in 300 ml of chloroform, and 70 g of silica gel was then added to and dispersed in the above solution, a filtrate obtained by filtration was concentrated and then dispersed in and washed with 50 ml of methanol. Subsequently, this methanol solution was dried at 80° C. under a reduced pressure, so that 2.00 g (yield: 81.0%) of a yellow crystal was obtained.

It was confirmed by a mass spectrometry that M+ of this compound was 678.

In addition, it was also confirmed by NMR measurement that the mixing ratio between the example compounds D27 and D28 was 1:1.

$^1$H-NMR (CDCl$_3$): δ (ppm)=8.67 (d, 2H, J=8.0), 8.61 (d, 2H, J=7.6), 8.51 (d, 2H, J=8.4), 8.45 (d, 2H, J=8.4), 8.20-8.04 (m, 14H), 7.99-7.959 (m, 4H), 7.91-7.84 (m, 8H), 7.79 (t, 2H, J=7.6), 7.73-7.64 (m, 8H), 7.60-7.52 (m, 4H), 6.82 (s, 2H), 6.63 (d, 2H, J=7.6)

According to the result of measurement of photoluminescence at an excitation wavelength of 347 nm using F-5400 manufactured by Hitachi, Ltd., the light emission spectrum of a toluene solution containing the mixture of the example compounds D27 and D28 at a concentration of $1.0 \times 10^{-6}$ mol/L was a blue light emission spectrum having a maximum intensity at an emission peak of 453 nm.

Example 2

Synthesis of Example Compounds D29 and D30

In accordance with the method described below, example compounds D29 and D30 were synthesized. For the synthesis, the synthetic route 3 was used.

Synthetic Route3
[Chem. 29]

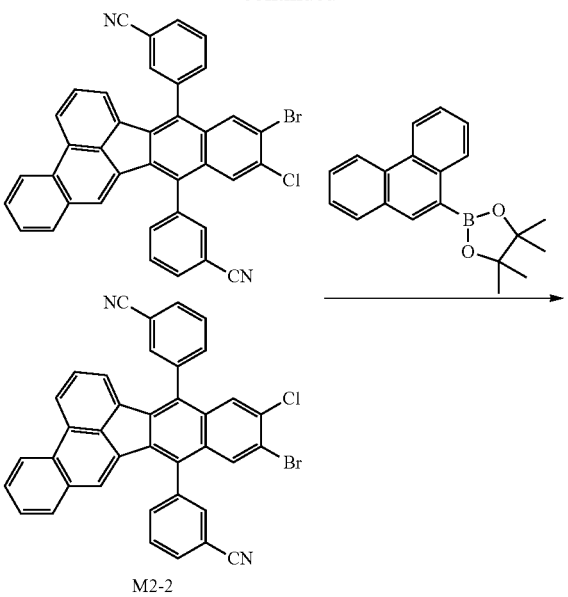

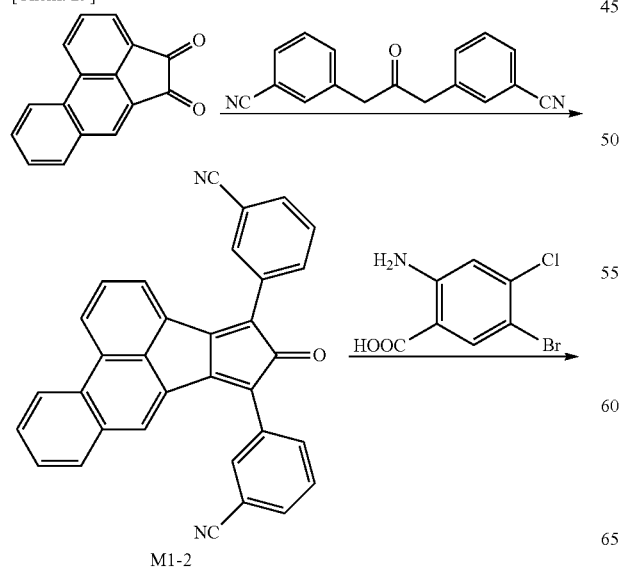

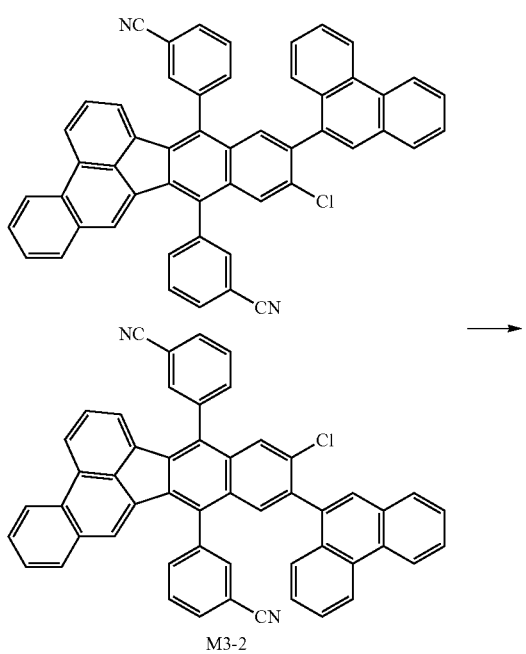

(2) Synthesis of Intermediate M2-2

[Chem. 31]

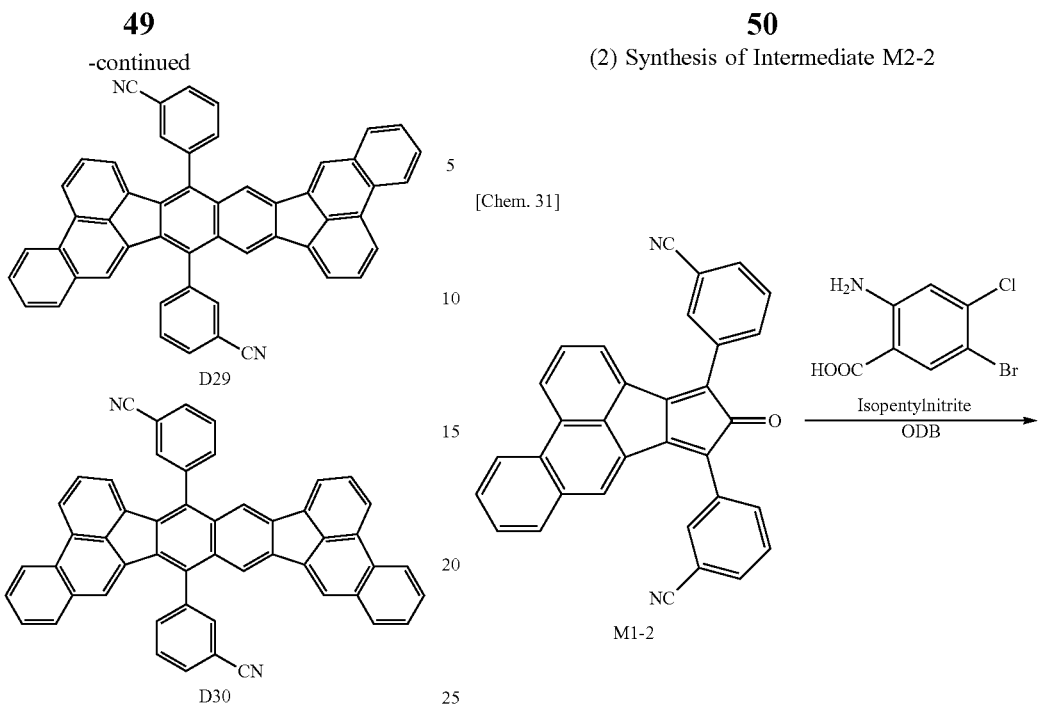

(1) Synthesis of Intermediate M1-2

[Chem. 30]

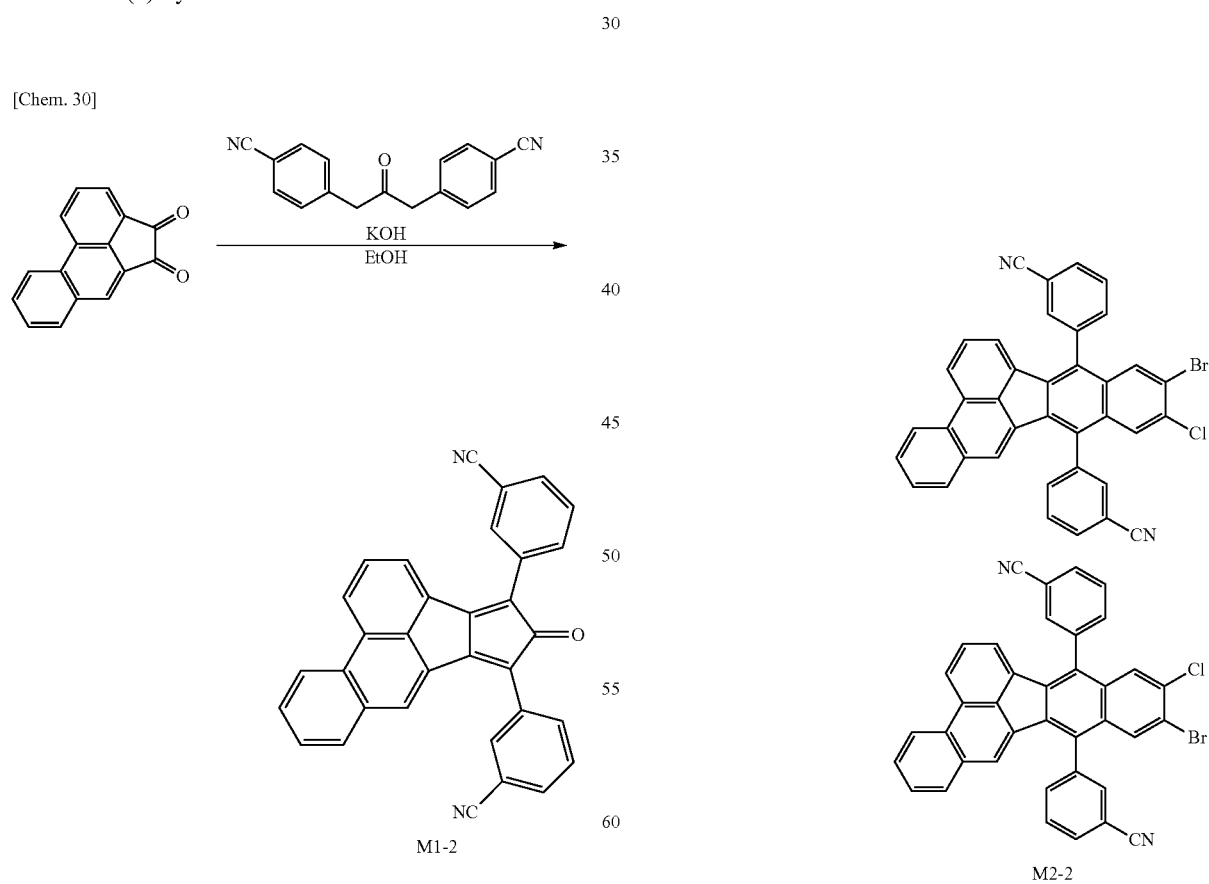

Synthesis was performed in a manner similar to that for the intermediate M1-1 except that 4,4'-(2-oxopropane-1,3-diyl)dibenzonitrile was changed to 3,3'-(2-oxopropane-1,3-diyl)dibenzonitrile.

Synthesis was performed in a manner similar to that for the intermediate M2-1 except that the intermediate M1-1 was changed to the intermediate M1-2.

(3) Synthesis of Intermediate M3-2

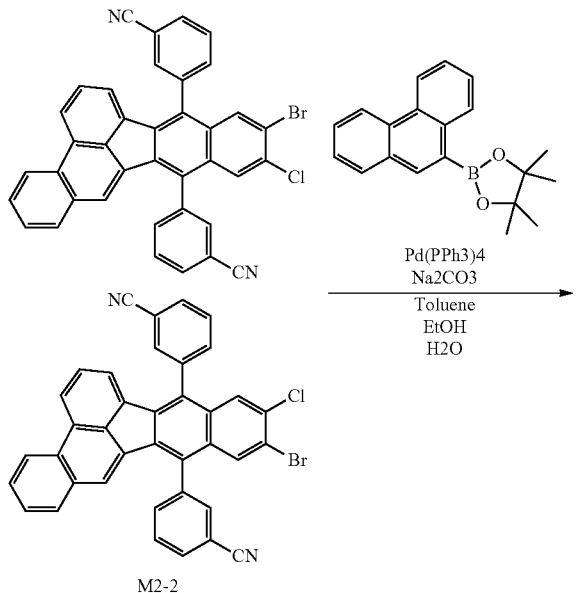

Synthesis was performed in a manner similar to that for the intermediate M3-1 except that the intermediate M2-1 was changed to the intermediate M2-2.

(4) Synthesis of Example Compounds D29 and D30

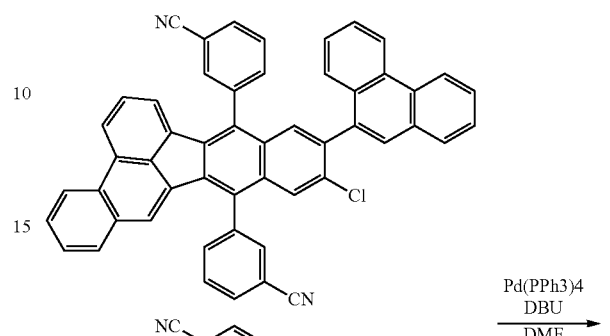

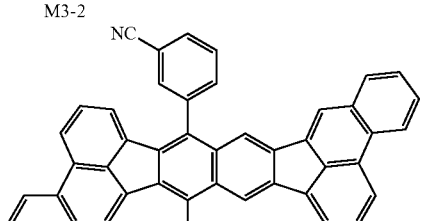

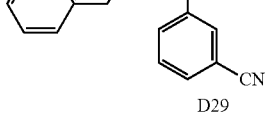

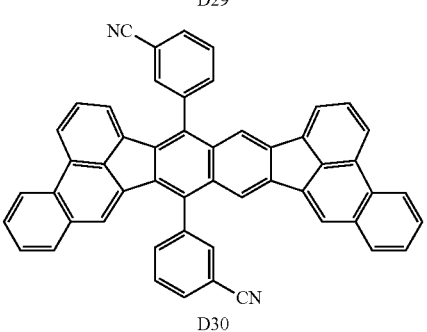

Synthesis was performed in a manner similar to that for the example compounds D27 and D28 except that the intermediate M3-1 was changed to the intermediate M3-2.

It was confirmed by a mass spectrometry that M+ of this compound was 678.

In addition, it was also confirmed by NMR measurement that the mixing ratio between the example compounds D29 and D30 was 1:1.

$^1$H-NMR (CDCl$_3$): δ (ppm)=8.67 (d, 2H, J=8.4), 8.61 (d, 2H, J=8.0), 8.5 (dd, 2H, J=8.0), 8.45 (d, 2H, J=8.0), 8.22-

8.21 (m, 2H), 8.17-7.91 (m, 24H), 7.79 (t, 2H, J=7.2), 7.73-7.64 (m, 8H), 7.59-7.51 (m, 4H), 6.76 (s, 2H), 6.57 (d, 2H, J=7.2)

According to the result of measurement of photoluminescence at an excitation wavelength of 412 nm using F-5400 manufactured by Hitachi, Ltd., the light emission spectrum of a toluene solution containing the mixture of the example compounds D29 and D30 at a concentration of $1.0 \times 10^{-6}$ mol/L was a blue light emission spectrum having a maximum intensity at an emission peak of 453 nm.

Comparative Example 1

As a comparative example, a comparative compound A1 represented by the following structural formula was synthesized, and based on the measurement of photoluminescence and absorption spectrum, comparison of the quantum yield was performed. For the absorption spectrum, UV-570 manufactured by JASCO Corp. was used. The quantum yield of the comparative compound A1 was regarded as 1.00, and a relative intensity was calculated.

The quantum yield of the following compound A1 (7,16-diphenylfluorantheno[8,9-k]fluoranthene) used for the comparative example was regarded as 1.00, and a relative intensity was calculated. The results are shown in Table 3.

[Chem. 34]

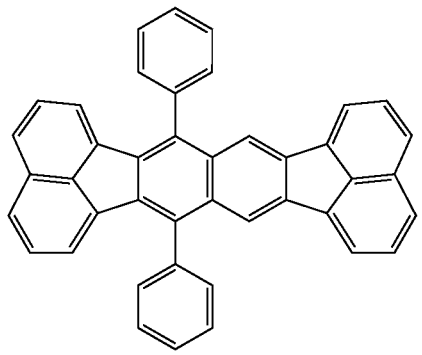

A1

TABLE 3

| | | LIGHT EMISSION WAVELENGTH [nm] | QUANTUM YIELD |
|---|---|---|---|
| EXAMPLE 1 | D27, D28 | 453 | 1.18 |
| EXAMPLE 2 | D29, D30 | 453 | 1.12 |
| COMPARATIVE EXAMPLE 1 | A1 | 458 | 1.00 |

Accordingly, it was found that the fused polycyclic compound of this embodiment can obtain a high quantum yield while emitting blue light.

Examples 3 to 10

In the examples, an anode, a hole injection layer, a hole transport layer, a light emitting layer, a hole-exciton block layer, an electron transport layer, and a cathode were sequentially formed on a substrate by the following methods, so that an organic light emitting element was formed.

A film functioning as an anode and having a thickness of 100 nm formed on a glass substrate using ITO by a sputtering method was used as a transparent conductive support substrate (ITO substrate).

On this ITO substrate, the following organic compound layers and electrode layers were sequentially formed by vacuum deposition with resistance heating in a vacuum chamber at a pressure of $10^{-5}$ Pa. In this case, the electrodes were formed so that the areas thereof facing each other were each set to 3 mm$^2$. The reason two types of guest materials were present is that isomers having different substitution positions were used at a mixing ratio of 1:1.

A general structure of the light emitting layer studied in this embodiment is shown below.

Hole injection layer (65 nm) G1
Hole transport layer (45 nm) G2
Light emitting layer (25 nm) Host: G3, Guest: example compounds shown in Table 3 (weight ratio: 1%)
Hole-exciton block layer (5 nm) G4
Electron transport layer (20 nm) G5
Metal electrode layer 1 (0.5 nm) LiF
Metal electrode layer 2 (100 nm) Al For each layer, an appropriate material was selected from the compounds shown in Table 4.

TABLE 4

| COMPOUND |
|---|
| G1 |

TABLE 4-continued
| COMPOUND |
|---|
| G2 G2-1 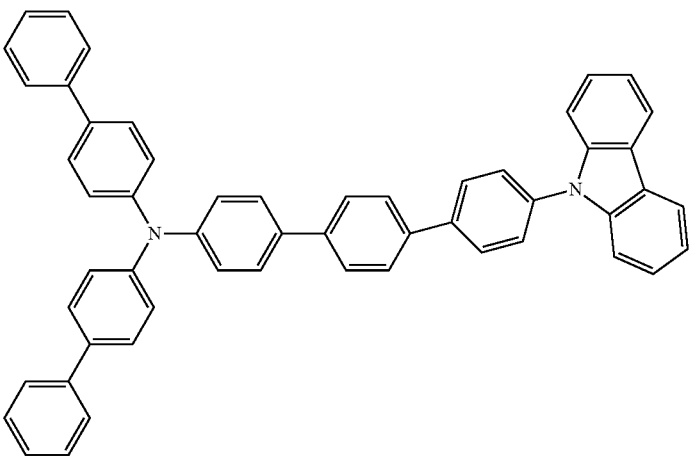 [SMILES: c1ccc(-c2ccc(N(c3ccc(-c4ccccc4)cc3)c3ccc(-c4ccc(-c5ccc(-n6c7ccccc7c7ccccc76)cc5)cc4)cc3)cc2)cc1] |
| G2-2 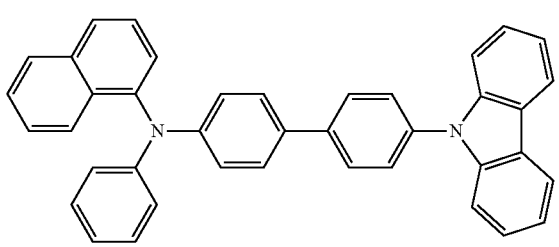 [SMILES: c1ccc(N(c2ccc(-c3ccc(-n4c5ccccc5c5ccccc54)cc3)cc2)c2cccc3ccccc23)cc1] |
| G3 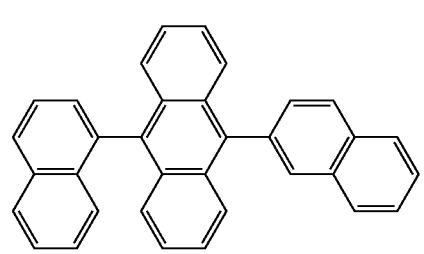 [SMILES: c1ccc2cc(-c3c4ccccc4c(-c4cccc5ccccc45)c4ccccc34)ccc2c1] |
| G4 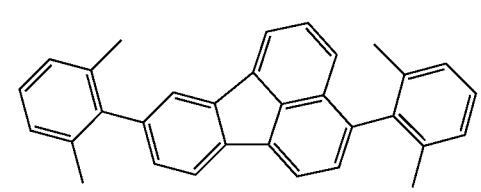 [SMILES: Cc1cccc(C)c1-c1ccc2c(c1)-c1cccc3c(-c4c(C)cccc4C)ccc-2c13] |

TABLE 4-continued

| COMPOUND |
|---|

G5  G5-1
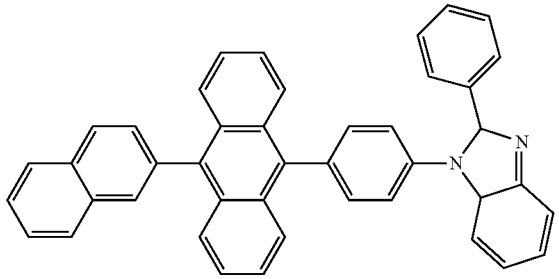 [SMILES: C1=CC2=NC(c3ccccc3)N(c3ccc(-c4c5ccccc5c(-c5ccc6ccccc6c5)c5ccccc45)cc3)C2C=C1]

G5-2
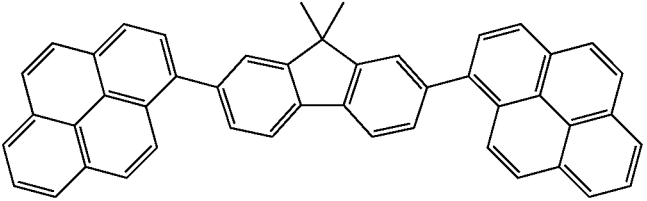 [SMILES: CC1(C)c2cc(-c3ccc4ccc5cccc6ccc3c4c56)ccc2-c2ccc(-c3ccc4ccc5cccc6ccc3c4c56)cc21]

G5-3
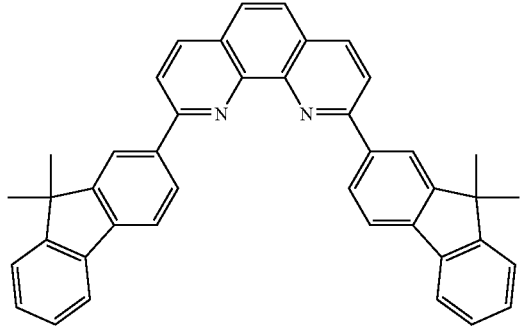

As for the properties of the organic light emitting element, current-voltage properties were measured using a microammeter 4140B manufactured by Hewlett-Packard Co., and the light emission luminance was measured using SR3 manufactured by Topcon Corp.

The properties of the organic light emitting elements of Examples 3 to 10 are shown in Table 5.

TABLE 5

|  | GUEST | HOLE TRANSPORT LAYER | ELECTRON TRANSPORT LAYER | EXTERNAL QUANTUM EFFICIENCY @1000 cd/m2 | HALF-LIFE [h] @100 mA/cm2 | CIE CHROMATICITY (X, Y) |
|---|---|---|---|---|---|---|
| EXAMPLE 3 | D27, D28 | G2-1 | G5-1 | 9.2 | 1,081 | (0.13, 0.14) |
| EXAMPLE 4 | D27, D28 | G2-2 | G5-1 | 9.3 | 1,053 | (0.13, 0.15) |
| EXAMPLE 5 | D27, D28 | G2-2 | G5-1(30) | 9.3 | 864 | (0.14, 0.15) |
| EXAMPLE 6 | D27, D28 | G2-2 | G5-2(20)/G5-3(5) | 8.5 | 853 | (0.14, 0.14) |
| EXAMPLE 7 | D29, D30 | G2-1 | G5-1 | 8.9 | 548 | (0.14, 0.17) |
| EXAMPLE 8 | D29, D30 | G2-2 | G5-1 | 9.7 | 288 | (0.14, 0.15) |
| EXAMPLE 9 | D29, D30 | G2-2 | G5-1(30) | 9.4 | 320 | (0.14, 0.17) |
| EXAMPLE 10 | D29, D30 | G2-2 | G5-2(20)/G5-3(5) | 8.8 | 479 | (0.14, 0.17) |

(note 1)
electron transport layer: the number in the parentheses ( ) indicates the thickness of the layer, and when no parentheses are shown, the thickness of the layer is 20 nm.

The organic compound of the present invention is a novel compound which has a high quantum yield and which emits light suitable for blue color, and when this organic compound is used for an organic light emitting element, an organic light emitting element having a high luminance and a long durability life can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-027778, filed Feb. 15, 2013, which is hereby incorporated by reference herein in its entirety.

REFERENCE SIGNS LIST

8 TFT element
11 anode
12 organic compound layer
13 cathode

The invention claimed is:

1. A fused polycyclic compound represented by the following general formula [1] or [2]:

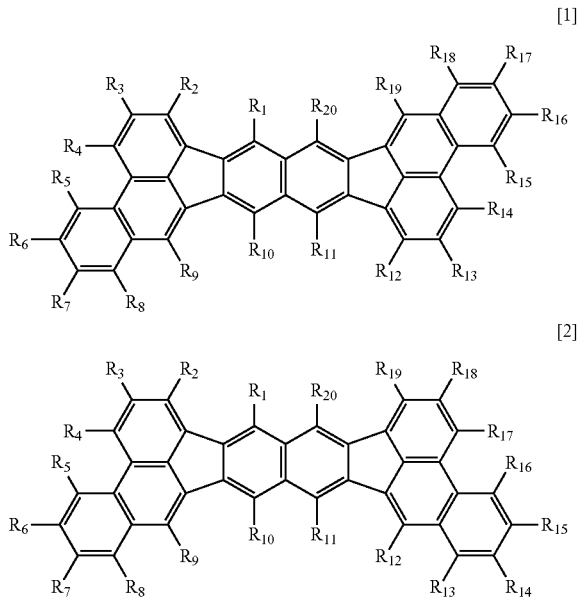

wherein in the general formulas [1] and [2], $R_1$ to $R_{20}$ are each independently selected from the group consisting of a hydrogen atom, a cyano group, a substituted or an unsubstituted alkyl group, a substituted or an unsubstituted aryl group, and a substituted or an unsubstituted heterocyclic group.

2. The fused polycyclic compound according to claim 1, wherein at least two of $R_1$, $R_{10}$, $R_{11}$, and $R_{20}$ are independently selected from the group consisting of a cyano group, a substituted or an unsubstituted alkyl group, a substituted or an unsubstituted aryl group, and a substituted or an unsubstituted heterocyclic group.

3. The fused polycyclic compound according to claim 1, wherein at least two of $R_1$, $R_{10}$, $R_{11}$, and $R_{20}$ each represent an electron withdrawing substituent.

4. The fused polycyclic compound according to claim 3, wherein the electron withdrawing substituent is a phenyl group, a pyridyl group, a quinolinyl group, or an isoquinolinyl group, and
the phenyl group has a halogen atom, a halogenated alkyl group, a cyano group, or a benzimidazole group.

5. The fused polycyclic compound according to claim 2, wherein two of $R_1$, $R_{10}$, $R_{11}$, and $R_{20}$ each represent a hydrogen atom.

6. The fused polycyclic compound according to claim 2, wherein $R_1$ and $R_{10}$ or $R_{11}$ and $R_{20}$ each represent a hydrogen atom.

7. The fused polycyclic compound according to claim 1, wherein the fused polycyclic compound emits blue light.

8. An organic light emitting element comprising:
a pair of electrodes; and
an organic compound layer provided between the electrodes,
wherein the organic compound layer contain the fused polycyclic compound according to claim 1.

9. The organic light emitting element according to claim 8,
wherein the organic compound layer includes a light emitting layer containing a host and a guest, and
the guest includes the fused polycyclic compound.

10. The organic light emitting element according to claim 8,
wherein the organic light emitting element emits blue light.

11. The organic light emitting element according to claim 8,
wherein the organic light emitting element emits white light,
the organic compound layer contains at least two types of light emitting materials,
one of the at least two types of light emitting materials includes the fused polycyclic compound, and
at least one of the at least two types of light emitting materials emits light different from that of the at least two types of light emitting materials.

12. The organic light emitting element according to claim 8,
wherein the organic light emitting element emits white light,
the organic compound layer includes a plurality of light emitting layers,
one of the light emitting layers contains the fused polycyclic compound, and
at least one of the light emitting layers emits light different from that of the other light emitting layers.

13. An organic light emitting element comprising:
a pair of electrodes; and
an organic compound layer provided between the electrodes,
wherein the organic compound layer contain the fused polycyclic compounds represented by the general formulas [1] and [2] according to claim 1.

14. A display device comprising:
a plurality of pixels, the display device performing display by controlling light emission of the pixels,
wherein at least one of the pixels includes the organic light emitting element according to claims 8 and an active element connected thereto.

15. An image information processing device comprising:
an input portion to which image information is input; and
a display portion which displays an image, wherein the display portion includes the display device according to claim 14.

16. A lighting device comprising:
the light emitting element according to claim 8; and
an AC/DC converter circuit connected thereto.

17. An image forming device comprising:
a photoreceptor;
a charging portion charging the photoreceptor;
an exposure portion exposing the photoreceptor to form an electrostatic latent image; and
a developer developing the electrostatic latent image formed on the photoreceptor,
wherein the exposure portion includes the organic light emitting element according to claim 8.

18. An exposure device which exposes a photoreceptor, the exposure device comprising:
the organic light emitting element according to claim 8; and
an active element connected thereto.

19. The exposure device according to claim 18,
wherein the organic light emitting elements are arranged along a long axis direction of the photoreceptor to form lines.

20. A lighting device comprising:
the organic light emitting element according to claim 13; and
an AC/DC converter circuit connected thereto.

* * * * *